United States Patent
Markovic et al.

(10) Patent No.: US 10,073,701 B2
(45) Date of Patent: Sep. 11, 2018

(54) SCALABLE AND PARAMETERIZED VLSI ARCHITECTURE FOR COMPRESSIVE SENSING SPARSE APPROXIMATION

(71) Applicant: The Regents of the University of California, Oakland, CA (US)

(72) Inventors: Dejan Markovic, Los Angeles, CA (US); Fengbo Ren, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 564 days.

(21) Appl. No.: 14/446,272

(22) Filed: Jul. 29, 2014

(65) Prior Publication Data

US 2015/0032990 A1 Jan. 29, 2015

Related U.S. Application Data

(60) Provisional application No. 61/859,628, filed on Jul. 29, 2013.

(51) Int. Cl.
*G06F 9/38* (2018.01)
*G16H 40/63* (2018.01)

(52) U.S. Cl.
CPC .......... *G06F 9/3893* (2013.01); *G16H 40/63* (2018.01)

(58) Field of Classification Search
CPC ............... G06F 9/3893; G06F 9/30036; G06F 9/30065; G06F 9/3004; H03M 7/3062
See application file for complete search history.

(56) References Cited

U.S. PATENT DOCUMENTS

| | | | |
|---|---|---|---|
| 5,499,192 A | * | 3/1996 | Knapp ................ G06F 17/5054 716/102 |
| 9,870,338 B2 | * | 1/2018 | Ould-Ahmed-Vall ...................... G06F 15/78 |

OTHER PUBLICATIONS

Depeng Yang, Husheng Li, Gregory D. Peterson and Aly Fathy, "Compressed Sensing Based UWB Receiver Hardware Compressing and FPGA Reconstruction" published in: Information Sciences and Systems, 2009. CISS 2009. 43rd Annual Conference, on Mar. 18-20, 2009).*

(Continued)

*Primary Examiner* — Keith E Vicary
*Assistant Examiner* — Emily E Larocque
(74) *Attorney, Agent, or Firm* — KPPB LLP

(57) ABSTRACT

Systems and methods for implementing a scalable very-large-scale integration (VLSI) architecture to perform compressive sensing (CS) hardware reconstruction for data signals in accordance with embodiments of the invention are disclosed. The VLSI architecture is optimized for CS signal reconstruction by implementing a reformulation of the orthogonal matching pursuit (OMP) process and utilizing architecture resource sharing techniques. Typically, the VLSI architecture is a CS reconstruction engine that includes a vector and scalar computation cores where the cores can be time-multiplexed (via dynamic configuration) to perform each task associated with OMP. The vector core includes configurable processing elements (PEs) connected in parallel. Further, the cores can be linked by data-path memories, where complex data flow of OMP can be customized utilizing local memory controllers synchronized by a top-level finite-state machine. The computing resources (cores and data-paths) can be reused across the entire OMP process resulting in optimal utilization of the PEs.

16 Claims, 18 Drawing Sheets

(56) References Cited

OTHER PUBLICATIONS

Xilinx, inc. "XC4000E/XL FPGAs Description—Product Obsolete" May 14, 1999 (Version 1.6), published on https://www.xilinx.com/support/documentation/data_sheets/4000.pdf.*

Fulvio Moschetti, Lorenzo Granai, Pierre Vandergheynst and Pascal Frossara "New Dictonary and Fast Atom Searching Method for Matching Pursuit Representation of Displaced Frame Difference" published in: Image Processing. 2002. Proceedings. 2002 International conference, on Sep. 22-25, 2002.*

Shaojun Wang, Yu Peng, Guangquan Zhao and Xiyuan Peng "Accelerating On-Line Training of LS-SVM with Run-Time Reconfiguration" published in: Field-Programmable Technology (FPT), 2011 International Conference, on Dec. 12-14, 2011.*

Bai et al., "High-Speed Compressed Sensing Reconstruction on FPGA Using OMP and AMP", 2012 19th IEEE International Conference on Electronics, Circuits, and Systems (ICECS 2012), Dec. 2012, pp. 53-56.

Candes, J. et al., "An Introduction to Compressive Sampling", IEEE Signal Processing Magazine, vol. 25, Issue 2, Mar. 2008, Retrieved from http://authors.library.caltech.edu/10092/1/CANieeespm08.pdf, pp. 21-30.

Duarte et al., "Single-Pixel Imaging via Compressive Sampling", IEEE Signal Processing Magazine, vol. 83, Mar. 2008, pp. 83-91.

Maechler et al., "Matching Pursuit: Evaluation and Implementation for LTE Channel Estimation", Proceedings of 2010 IEEE International Symposium on Circuits and Systems, May 30-Jun. 2, 2010, pp. 589-592.

Maechler et al., "VLSI Design of Approximate Message Passing for Signal Restoration and Compressive Sensing", IEEE Journal on Emerging and Selected Topics in Circuits and Systems, Oct. 2012, vol. 2, No. 3, pp. 1-11.

Moody et al., "The Impact of the MIT-BIH Arrhythmia Database", IEEE Engineering in Medicine and Biology, May/Jun. 2001, pp. 45-50.

Septimus et al., "Compressive Sampling Hardware Reconstruction", Proceedings of 2010 IEEE International Symposium on Circuits and Systems, May 30-Jun. 2, 2010, pp. 3316-3319.

Stanislaus et al., "High Performance Compressive Sensing Reconstruction Hardware with QRD Process", 2012 IEEE International Symposium on Circuits and Systems, May 2012, pp. 29-32.

Tropp et al., "Signal Recovery from Random Measurements Via Orthogonal Matching Pursuit", IEEE Transactions on Information Theory, Dec. 2007, vol. 53, No. 12, pp. 4655-4666.

Yang, "Turbo Bayesian Compressed Sensing", Thesis, University of Tennessee, Knoxville, Aug. 2011, 175 pgs.

* cited by examiner

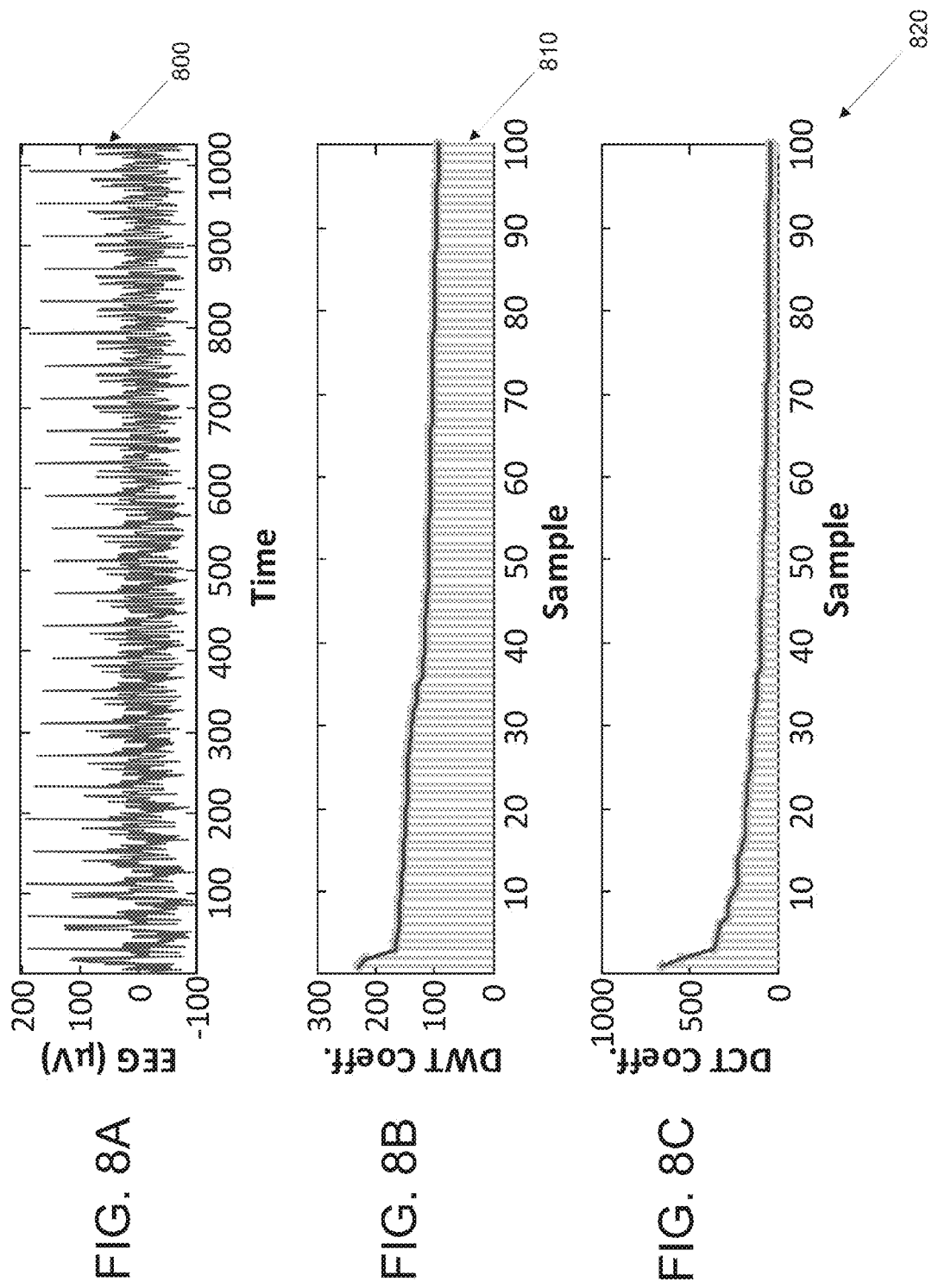

SCALABLE AND PARAMETERIZED VLSI ARCHITECTURE FOR COMPRESSIVE SENSING SPARSE APPROXIMATION

CROSS-REFERENCE TO RELATED APPLICATIONS

This application claims priority to U.S. Provisional Patent Application No. 61/859,628 entitled "Scalable and Parameterized VLSI Architecture for Compressive Sensing Sparse Approximation", filed Jul. 29, 2013, the disclosure of which is incorporated herein by reference.

FIELD OF THE INVENTION

The present invention generally relates to very-large-scale integration (VLSI) architectures and specifically to VLSI architectures for compressive sensing sparse approximations.

BACKGROUND

The theory of compressive sensing, also known as compressed sensing or CS is a novel sensing/sampling paradigm that goes against the common wisdom in data acquisition. CS theory asserts that one can recover certain signals from far fewer samples or measurements than traditional methods that follow Shannon's theorem: the sampling rate must be at least twice the maximum frequency present in the signal (the so-called Nyquist rate). Alternatively, the sampling rate required by CS is directly proportional to the sparsity level of the signal on a proper basis. To make this possible, CS relies on two principles: sparsity, which pertains to the signals of interest (usually on a selective basis), and incoherence, which pertains to the sensing modality.

Sparsity expresses the idea that the "information rate" of a continuous time signal may be much smaller than suggested by its bandwidth, or that a discrete-time signal depends on a number of degrees of freedom, which is comparably much smaller than its (finite) length. Sparsity says that objects have a sparse representation in one domain can be spread out in the domain in which they are acquired, such as a Dirac or spike in the time domain can be spread out in the frequency domain. More precisely, CS exploits the fact that many natural signals are sparse or compressible in the sense that they have concise representations when expressed on an appropriate basis.

Incoherence extends the duality between time and frequency. Incoherence says that each measurement of the signal should have low or limited correlation between all the other measurements regardless of the signal basis such that each measurement can carry enough new information about the signal, or in other words, the measurements carry limited mutual information. Therefore, the redundancy in the measurements is limited, and the sampling rate required is directly proportional to the amount of information desired regardless of the signal basis. Incoherence extends the proportionality between the sampling rate and the signal information to an arbitrary basis, unlike the Nyquist rate, which is proportional to the signal information on Fourier basis only.

According to the theory of CS, one can design efficient sensing or sampling protocols that capture the useful information content embedded in a sparse signal and condense it into a small amount of data. These protocols are nonadaptive and simply involve correlating the signal with randomness that are incoherent with the sparsifying basis. What is most remarkable about these sampling protocols is that they allow a sensor to very efficiently capture the information in a sparse signal without trying to comprehend the signal. Further, there is a way to use numerical optimization to reconstruct the full-length signal from the small amount of collected data. In other words, systems based on CS principles can sample—in a signal independent fashion—at a low rate and later use computation power for reconstruction. Effectively, such systems sense and compress data simultaneously (thus the name compressed sensing).

CS has received significant research attention due to its insights into sampling and signal processing. The CS framework offers an approach for compressive data sampling at sub-Nyquist rates, which may lower power consumption and the costs associated with data acquisition systems for a variety of signals. CS techniques have shown promising results in a wide range of applications, including the data acquisition in bio-medical applications, such as (but not limited to) magnetic resonance imaging (MRI), electrocardiogram (ECG), and electroencephalogram (EEG).

However, CS techniques in real applications still face significant challenges. For example, the digital reconstruction in CS typical involves solving an optimization problem using either greedy heuristics or convex relaxations. The computational complexity of these processes is usually 1-2 orders of magnitude higher than the orthogonal transform used in the Nyquist framework. This can lead to a low efficiency of real-time processing on general purpose processors, limiting the application of CS techniques on mobile platforms. An efficient hardware solution may benefit a variety of CS applications in terms of cost, portability, and battery-life.

SUMMARY OF THE INVENTION

Systems and methods for implementing a scalable very-large-scale integration (VLSI) architecture to perform compressive sensing (CS) hardware reconstruction for data signals in accordance with embodiments of the invention are disclosed. In one embodiment, an integrated circuit architecture for CS reconstruction includes a vector computation core includes a plurality of processing elements inter-connected in parallel that can be configured to perform vector operations, a scalar computation core configured to perform scalar operations, a shift register logic configured to provide optional latency in feedback paths associated with the plurality of processing elements and in a feedback path between the vector and scalar computation cores, a plurality of data-path memories each comprising a memory controller and configured to connect the vector and scalar computation cores, where the plurality of data-path memories are configured to provide data-flow control using the plurality of memory controllers and the plurality of data-path memories includes: at least one data-path memory configured to receive and store CS sampled input data, at least one data-path memory configured to store an active set of values, at least one data-path memory configured to store a residual error estimate, and at least one data-path memory configured to store an estimated output data signal, and a global control unit configured to synchronize and coordinate the plurality of memory controllers to jointly perform a selective set of vector and scalar operations using a first atom searching configuration of the vector and scalar computation cores, and the plurality of data-path memories in which a single atom is selected by maximizing its correlation coefficients with the residual error estimate and added to the active set of values associated with the estimated output data signal, a second least squares solving configuration in which the shift register logic, the vector and scalar computation cores, and the plurality of data-path memories are configured to solve a series of linear equations relating the output data signal to the CS sampled input data to determine updates for the estimated output data signal that minimizes an error measure determined using the updated estimated output data signal and the CS sampled input data, and a third estimation update configuration of the vector and scalar computation cores, and the plurality of data-path memories, in which an output data signal estimate is updated based upon the solution to the series of linear equations and the residual error estimate, where the global control unit is configured to: set the residual error estimate to an initial value equal to the CS sampled input data, set the local controllers of the plurality of data-path memories and the vector and scalar computation cores to their initial states, and iterate between the first, second and third configurations until the updated residual estimate falls below a predetermined threshold.

In a further embodiment, the global control unit is a finite-state machine designed to synchronize and configure the memory controllers and the vector and scalar computation cores to iterate between the first, second and third configurations.

In another embodiment, the second least squares solving configuration solves the series of linear equations using a factorization method.

In a still another embodiment, the factorization method is an alternative Cholesky factorization, where the Cholesky factorization does not include a square root operation.

In a yet further embodiment, Cholesky factorization matrices are updated incrementally by computing at each iteration:

$$L_{t-1}D_{t-1}l_{21} = A_{\Lambda_{t-1}}^T a_\varphi$$

and $$d_{22} = a_\varphi^T a_\varphi - l_{21}^T D_{t-1} l_{21}$$

where $l_{21} \in \mathbb{R}^{t-1}$ is a column vector and $d_{22}$ is a scalar.

In a yet another embodiment, the plurality of processing elements inter-connected in parallel are dynamically configured using microcode generated by the global control unit.

In a further embodiment again, the scalar computation core comprises a comparator, a sequential divider, and a plurality of adders.

In another embodiment again, the selective set of scalar operations includes scalar comparison, addition, subtraction, accumulation, and division operations.

In another additional embodiment, the selective set of vector operations includes element-wise vector addition, multiplication, accumulation, multiply-accumulation, vector-scalar product, and inner product operations.

In a still yet further embodiment, the vector and scalar computation cores can be configured to cascade as a processing unit and configured to execute correlation sorting, folded inner product, forward substitution, and backward substitution operations.

In a still further embodiment again, the plurality of data-path memories each comprising a memory controller and configured to connect the vector and scalar computation cores further includes: at least one data-path memory configured to receive and store CS sampling matrix, at least one data-path memory configured to receive and store Cholesky factorization matrices, and at least one data-path memory configured to receive and store intermediate results.

In a still further additional embodiment, the global control unit is further configured to issue corresponding operation codes according to configurations to the local controllers of the plurality of data-path memories and the vector and scalar computation cores.

BRIEF DESCRIPTION OF THE DRAWINGS

FIGS. 8A-C are graphs illustrating an EEG signal and its associated coefficients in accordance with an embodiment of the invention.

DETAILED DESCRIPTION OF THE DRAWINGS

Figure 1A:
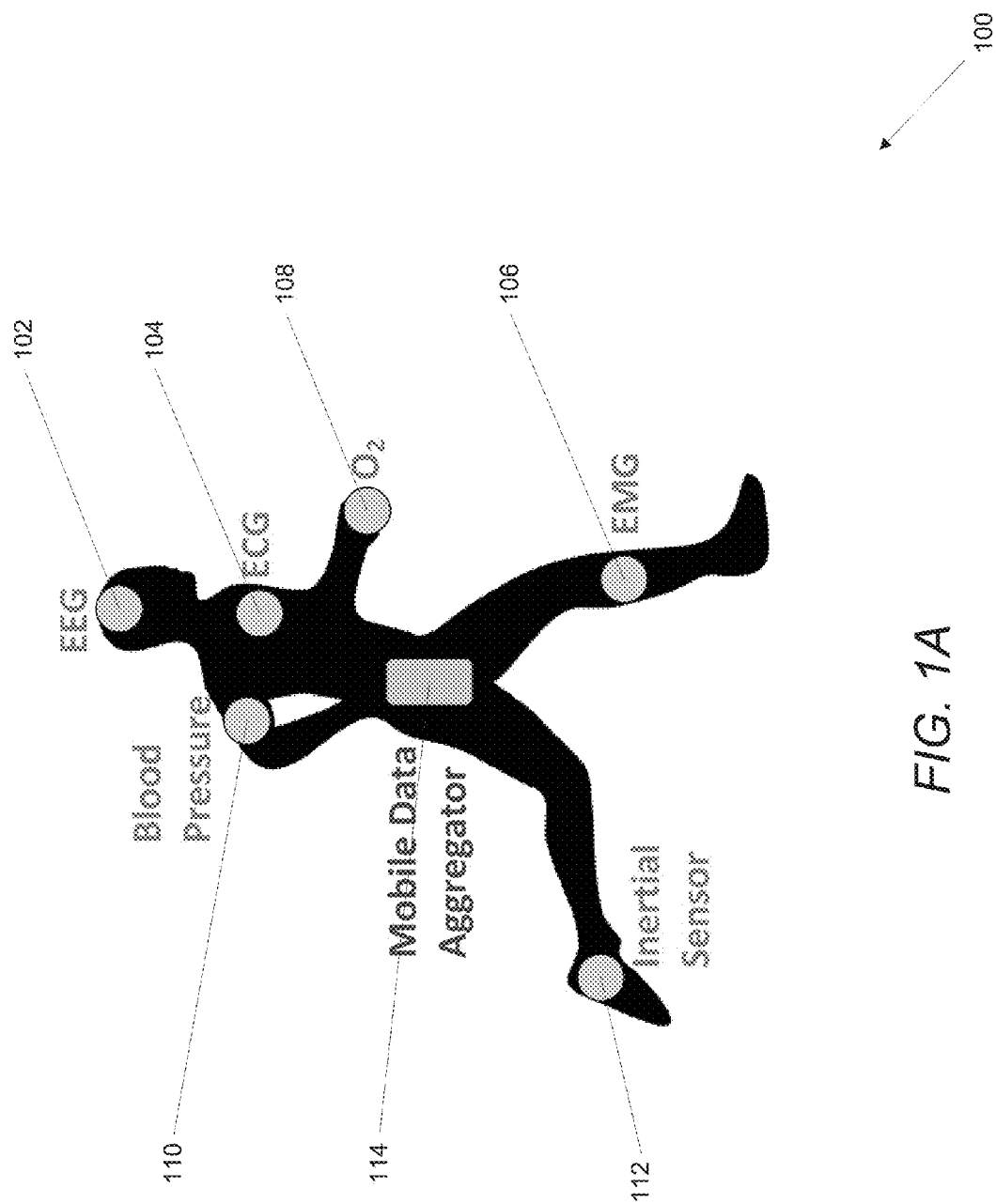
FIGS. 1A-C illustrate an on-body sensor network for performing continuous monitoring in accordance with an embodiment of the invention.

Turning now to the drawings, systems and methods for implementing a scalable very-large-scale integration (VLSI) architecture to perform compressive sensing (CS) hardware reconstruction for data signals. In several embodiments, the data signals can include (but are not limited to) bio-medical signals (i.e. signals that convey information related to physiology). In many embodiments, the VLSI architecture can be implemented in field programmable gate arrays (FPGAs) or system-on-chip (SOC) platforms. In various embodiments, the VLSI architecture is optimized for CS signal reconstruction by implementing a reformulation of the orthogonal matching pursuit (OMP) process and utilizing architecture resource sharing techniques as further disclosed below. In several embodiments, the VLSI architecture is a CS reconstruction engine that includes a vector and scalar computation cores where the cores can be time-multiplexed (via dynamic configuration) to perform each task associated with OMP. In many embodiments, the vector core includes configurable processing elements (PEs) connected in parallel. In a variety of embodiments, the cores are linked by data-path memories, where complex data flow of OMP can be customized utilizing local memory controllers synchronized by a top-level finite-state machine. In several embodiments, the computing resources (cores and data-paths) can be reused across the entire OMP process resulting in optimal utilization of the PEs.

In addition, the VLSI architecture can support a floating-point data format to accommodate various design parameters. In many embodiments, the floating-point data format provides dynamic range capability and flexibility for application specific customization. In several embodiments, the proposed architecture is independent of the data format of the arithmetic units in the design. Although floating-point may be utilized for general reconstruction purposes, a fixed point data format can also be applied to the same architecture when the dynamic range is limited in a specific application. Thus, in many embodiments, both floating and fixed point data formats can be accommodated.

In various embodiments, the VLSI architecture can be implemented on a Xilinx KC705 evaluation platform and tested with a variety of bio-signals and parameters. On-board evaluation results show that an FPGA implementation in accordance with embodiments of the invention, achieves similar levels of accuracy as a double-precision C program compiled to run on an Intel Core i7-4700MQ mobile process, while providing 47-147 times speed-up and 3-4 orders of magnitude better energy efficiency.

In discussing embodiments of the invention, the following notions will be observed. A matrix is denoted as an uppercase bold letter (e.g. A). A vector is denoted as a lower case letter (e.g. a). A lower case letter with a subscript when bolded (e.g. $\mathbf{a}_i$) represents the $i^{th}$ column vector of matrix A. A lower case letter with a subscript when not bolded (e.g. $a_i$,) represents an arbitrary vector indexed by i. x(i) represents the $i^{th}$ element of vector x. A set of index is denoted by an upper case Greek letter (e.g. $\Lambda$). $\mathbf{A}_\Lambda$, when bolded, represents the set of column vectors of A that are indexed by $\Lambda$, and x($\Lambda$) represents the set of elements of x that are indexed by set $\Lambda$.

Systems and methods for implementing a scalable very-large-scale integration (VLSI) architecture to perform compressive sensing (CS) hardware reconstruction for data signals in accordance with embodiments of the invention are discussed further below.

Signal Characteristics and Compressive Sensing
A. The Signal Sparsity

The sparsity of a signal is closely related to its $l_0$ pseudo-norm. The $l_0$ pseudo-norm of a signal $x \in \mathbb{R}^n$ is defined as $$\|x\|_0 = |\text{supp}(x)|, \tag{1}$$

where the operator $|\cdot|$ denotes the cardinality of a set and supp(x) is the support of x defined as $$\text{supp}(x) = \{i | x(i) \neq 0\}. \tag{2}$$

Namely, the $l_0$ pseudo-norm of x measures the number of non-zero elements in x. Unlike the other $l_p$ norms ($p \geq 1$), the $l_0$ pseudo-norm contains no information about the signal energy but indicates its sparsity level. A signal x is defined to be k-sparse if $\|x\|_0 \leq k$, and the set of all k-sparse signals in $\mathbb{R}^n$ can be denoted as $\mathbb{S}_k^n = \{x \in \mathbb{R}^n | \|x\|_0 \leq k\}$.

In practice, rare natural signals are ideally sparse on any basis due to the presence of noise. However, their sparse domain coefficients often exhibit a power-law decay. Specifically, given x is the coefficient of a signal $\alpha$ on the basis $\Phi$ as $\alpha = \Phi x$, the sorted coefficient x'=sort(x) often obeys a power-law decay given by $$|x'(i)| \leq C \cdot i^{-q}, \tag{3}$$

where C is a constant and q>0. Equation (3) indicates that a small portion of the coefficients often carry a significant portion of the signal energy on a proper basis. As a result, most natural signals are compressible, meaning that they can be well represented (with bounded errors) by a sparse coefficient vector on a proper basis.

B. CS Sampling and Reconstruction

A compressive sampling system can be modeled as a linear system given by $$y = \Theta\alpha + \beta, \tag{4}$$

where $\alpha \in \mathbb{R}^n$ is the signal, $\Theta \in \mathbb{R}^{m \times n}$ is the sampling matrix, $\beta \in \mathbb{R}^m$ is random noise with bounded energy $\|\beta\|_2 \leq \varepsilon$, and $y \in \mathbb{R}^m$ is the linear measurement or the sampled data. Given $\alpha = \Psi x$, (4) can also be represented as $$y = Ax + \beta, \tag{5}$$

where $A = \Theta\Psi \in \mathbb{R}^{m \times n}$. Note that in the context of compressive sampling, A is often a fat matrix with m<n, representing a dimensionality reduction from $\mathbb{R}^n$ to $\mathbb{R}^m$. Therefore, y is a compressed representation of the signal's sparse domain coefficients x that is encoded by A.

In order to recover x from y and then reconstruct $\alpha$, the linear equation in (5) is solved. Note that this is an underdetermined problem, which has infinite possible solutions. However, by utilizing the prior knowledge that x is sparse, it is possible to retrieve x by finding the sparsest solution of (5). It has been proven that a $x \in \mathbb{S}_k^n$ can be exactly recovered by solving $l_0$ pseudo-norm minimization given as $$\min\|x\|_0, \text{ subject to } \|y - Ax\|_2 \leq \varepsilon, \tag{6}$$

as long as A satisfies the Null Space Property (NSP) and the Restricted Isometry Property (RIP) of order 2k. It also has been proven that random matrices $A \in \mathbb{R}^{m \times n}$ generated from sub-Gaussian distributions, such as Gaussian or Bernoulli distributions, satisfy both the NSP and the RIP of order 2k, given $$m \geq C \cdot k \cdot \log\left(\frac{n}{k}\right), \tag{7}$$

where C is a constant.

The minimization problem in (6) is NP-hard. However, several greedy processes, such as orthogonal matching pursuit (OMP), have been proposed to solve it in a heuristic fashion. Another approach to solving this problem is to relax the objective function in (6) to its $l_1$ norm as $$\min\|x\|_1, \text{ subject to } \|y - Ax\|_2 \leq \varepsilon. \tag{8}$$

The formulation in (8) is also known as the basis pursuit denoising (BPDN) problem. It has been proven that the solution to (8) coincides with the solution to (6) with overwhelming probability. The BPDN problem in (8) is convex and can be solved through general convex optimization methods.

Wireless Healthcare Systems

Wireless healthcare technology can make medical resources, including medical facilities, medicine and professionals, more accessible. Such technology can assist in reducing medical costs while increasing the engagement between patients and doctors. Further, wireless healthcare can revolutionize the operational model of the medical system by transforming health related services from a system based on episodic examination, disease diagnosis and treatment, to one with continuous monitoring, disease prediction and prevention. However, a key challenge in wireless healthcare is efficient sensing technology including dealing with (i.e. transmission, storage and analysis) the enormous amount of data associated with continuous monitoring. In recent years, CS has received significant research attention due to its revolutionary insights into sampling and signal processing. As discussed above, the CS framework can offer a universal approach for compressive data sampling at sub-Nyquist rates resulting in less data while maintaining accuracy.

Figure 1B:
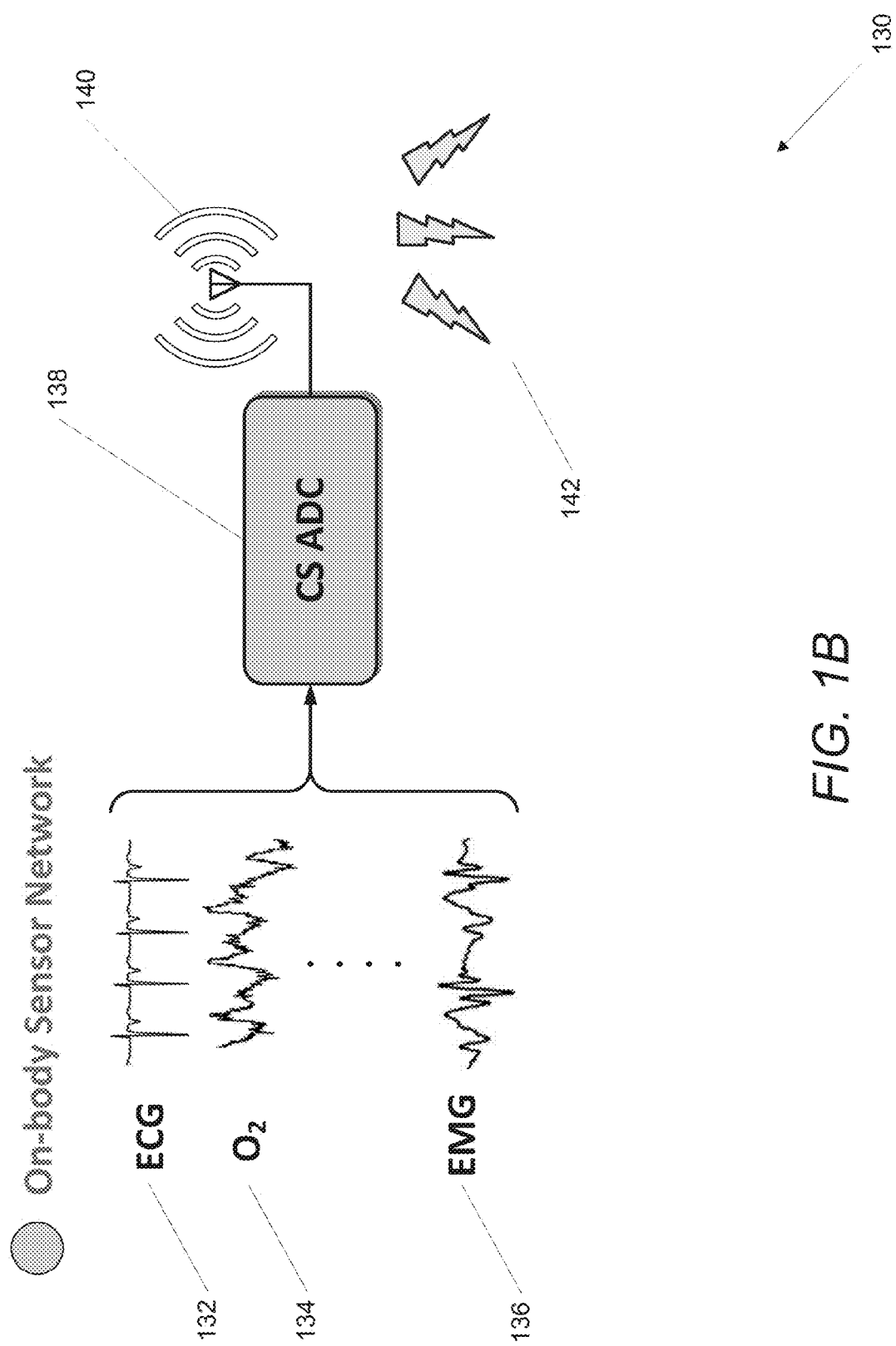
Figure 1C:
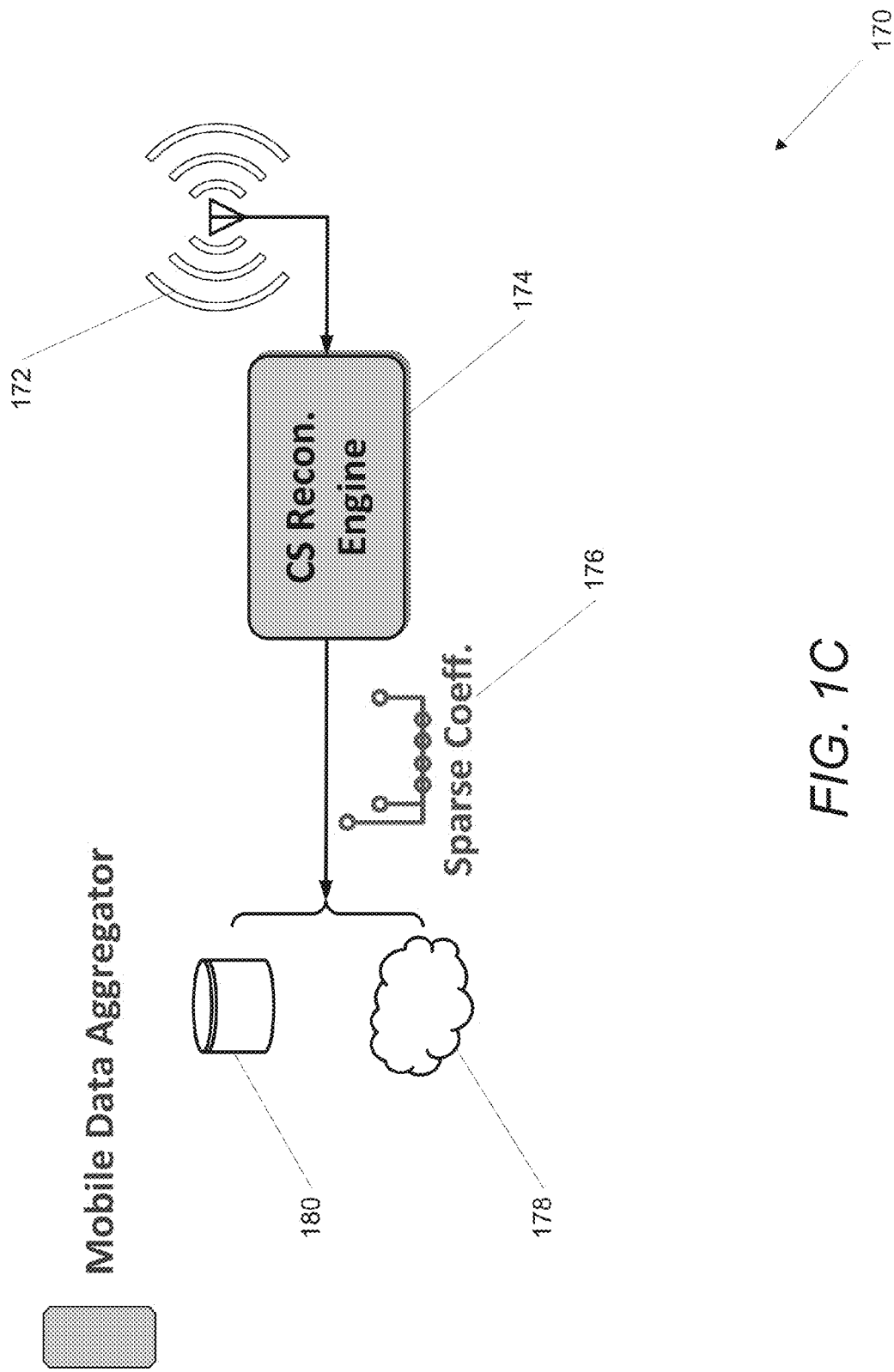

A system for a low-power and cost-effective on-body sensor network for performing continuous monitoring in wireless healthcare system in accordance with an embodiment of the invention is shown in FIGS. 1A-C. The on-body sensor system 100 can include various sensors that measure bio-medical signals including electroencephalogram (EEG) 102, electrocardiogram (ECG) 104, and electromyography (EMG) 106. In many embodiments, the on-body sensor system can also include sensors that measure oxygen concentration 108, blood pressure 110, and even an inertial sensor 112 to track movement. In several embodiments, the on-body sensor system can also include a mobile data aggregator 114 to perform real-time signal reconstruction (sparse coefficients only) as further discussed below.

A process for gathering data from the on-body sensor network in accordance with an embodiment of the invention is illustrated in FIG. 1B. The process 130 includes gathering data 132, 134, 136 generated from the various sensors and digitizing the data using an analog to digital converter (ADC) 138. In many embodiments, gathering data includes acquisition strategies that involve using CS implemented in manners familiar to one of ordinary skill in the art. In various embodiments, the digitized and compressively sampled data can be wirelessly transmitted 142 using a variety of transmit antennas 140 for further storage or processing.

A process for performing CS reconstruction in accordance with an embodiment of the invention is illustrated in FIG. 1C. The process 170 includes wirelessly receiving digitized sensor data using a variety of receive antennas 172. In many embodiments, the data can be processed using a CS reconstruction engine 174 to generate sparse coefficients 176 as further discussed below. The sparse coefficients 176 can be stored in a data storage device 180 or in a cloud based storage system 178. In several embodiments, the sparse coefficients and/or digitized sensor data can be further processed to make health related decision.

In various embodiments, the mobile data aggregator allows for on-site processing for making timely decisions. Further, it can also be beneficial where off-site processing is allowed since reconstructing the signal's sparse coefficients from the random measurements (sensor data) can further reduce the data size for on-site storage or transmission to the cloud. Although specific on-body sensor systems utilizing CS reconstruction engines are discussed above with respect to FIGS. 1A-C, any of a variety of on-body sensor systems including those with a variety of bio-medical sensors as appropriate to the requirements of a specific application can be utilized in accordance with embodiments of the invention. In many embodiments, the CS reconstruction engine can be optimized using VLSI architectures as disclosed below. Analysis and reformulation techniques of the CS reconstruction process in accordance with embodiments of the invention are discussed further below. Although discussed in the context of bio-medical systems, the VSLI architectures can be utilized to perform CS reconstruction processes in any of a variety of applications.

Analysis and Reformulation of the Reconstruction Process

It can be an extreme challenge to implement a traditional CS reconstruction engine on a limited resource platform (such as but not limited to) mobile platforms with limited power budgets. In particular, performing digital reconstruction in CS engines call for solving an optimization problem using either greedy heuristics (i.e. a process that follows the problem solving heuristic of making the locally optimal choice at each stage with the hope of finding a global optimum) or convex relaxation. The computational complexity of these techniques can be 1-2 orders of magnitude higher than that of orthogonal transforms used in the traditional Nyquist framework.

A. Orthogonal Matching Pursuit (OMP)

Typically, the optimization problem in CS reconstruction is solved using the greedy OMP process. Generally, OMP can efficiently solve the $l_0$ pseudo-norm minimization shown in (6). It is able to recover a k-sparse signal in exact k iterations with high probability. The concept of OMP is built upon the observation that when $x \in \mathbb{S}_k^n$ has only k non-zeros, the linear measurement $y=Ax$ can also be represented as $y=A_\Lambda x(\Lambda)$, where $\Lambda$, also known as the active set, is the index set of the non-zero elements in x. Therefore, to recover $x \in \mathbb{S}_k^n$, only $x(\Lambda)$ needs to be recovered. In many embodiments, given $A_\Lambda \in \mathbb{R}^{m \times k}$ and m>k, $x(\Lambda)$ can be best estimated by solving the least square (LS) problem given by $$\min \|y - A_\Lambda x(\Lambda)\|_2^2, \qquad (9)$$

as long as the active set can be identified. Consequently, identifying the correct active set can be a key task in performing OMP processes.

A pseudo-code of an OMP process in accordance with an embodiment of the invention is illustrated in Table I (reproduced below). In many embodiments, the process starts from an initial estimation $x_0 = \bar{0}$ and a residual $r_0 = y - Ax_0 = y$. In iteration t, the correlation coefficients of all the atoms in A and the current residual $r_{t-1}$ can be computed as $|A^T r_{t-1}|$.

In various embodiments, the index of the single atom that has the largest correlation coefficient can be added to the active set $\Lambda_{t-1}$, and a new estimation $x_t$ is made by solving the LS problem shown in (9) based on the updated $\Lambda_t$. Unless the estimation error $\|r_t\|_2$ meets the stopping criterion, iteration t+1 can be performed for a better estimation $x_{t+1}$. In several embodiments, in the OMP process, the size of the active set increases by one every iteration, and so does the sparsity level of x. This typically causes OMP to reconstruct x with as few elements as possible, thereby approaching the sparsest solution to (6). Although specific error measures for OMP processes are discussed above, any of a variety of error measures as appropriate to the requirements of a specific application can be utilized in accordance with embodiments of the invention.

TABLE I

PSEUDO-CODE OF THE OMP PROCESS

| Step | Operation |
|---|---|
| 1 | $r_0 = y, x_0 = \vec{0}, d = \vec{0}, \Lambda_0 = \emptyset, t = 1.$ |
| 2* | $c = A^T r_{t-1}, \varphi = \arg\max_i |c(i)|, \Lambda_t = \Lambda_{t-1} \cup \varphi.$ |
| 3 | $d(\Lambda_t) = \text{solve}_\alpha\{A_{\Lambda_t}^T A_{\Lambda_t} \alpha = c(\Lambda_t)\},$ |
| 4 | $r_t = r_{t-1} - A_{\Lambda_t} d(\Lambda_t), x_t = x_{t-1} + d, t = t + 1.$ |
| 5 | If $\|r_t\|_2 \leq \varepsilon$, stop, otherwise, go to step 2 |

*Assuming that all atoms in A are normalized.

B. Complexity Analysis of OMP

As shown in Table I, there are three main tasks performed in each iteration of OMP: atom searching (AS) for updating the active set (Table 1, step 2), least square (LS) solving for computing the updating direction (Table 1, step 3), and estimation update (EU) along the direction (table 1, step 4). Table II (reproduced below) summarizes the number of floating-point operations (FLOPs) that may be utilized in each task at iteration t, where t={1, 2, . . . , k} for $x \in \mathbb{S}_k^n$. In many embodiments, the FLOP count is calculated assuming that a Cholesky factorization is used for solving the LS problem in (9). In addition, the FLOP count can be calculated after the process reformulation toward resource sharing techniques as further presented below. As shown in Table II (reproduced below), the AS task constantly involves 2nm FLOPs in each iteration. In general CS problems, it is noted that n>m>>k. Consequently, the AS task contributes the most computation in OMP. On the other hand, the FLOPs utilized by the LS task increases quadratically with iteration t. However, regarding the condition of t≤k, it still has much less computation than the AS task due to the proper use of factorization techniques. Overall, the total computational complexity of OMP in k iterations can be estimated as 2 nmk+2mk²+k³.

Figure 2:
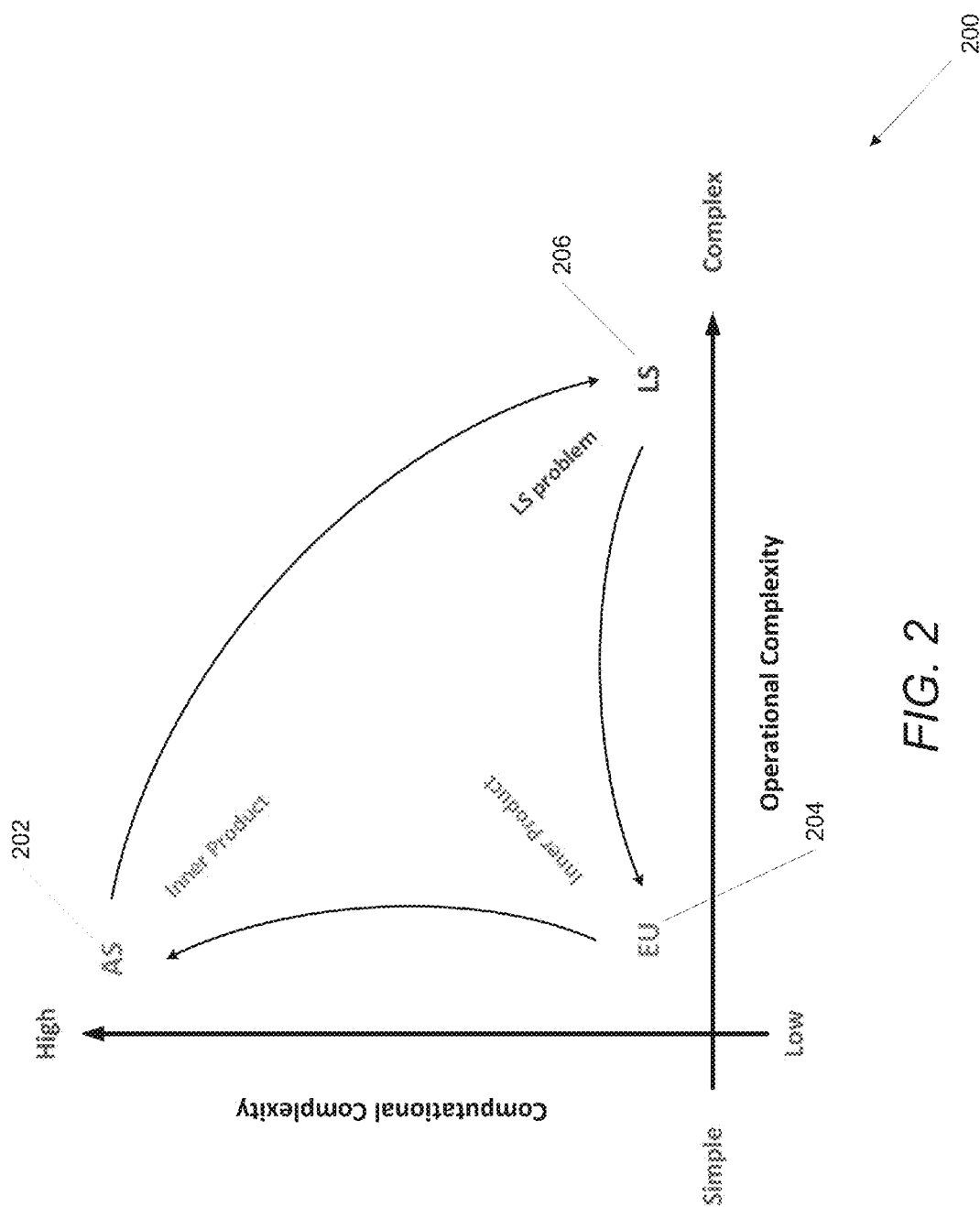
FIG. 2 is a graph of the complexity characteristics of tasks in an OMP process in accordance with an embodiment of the invention.

A graph illustrating the overall complexity characteristics of the OMP process in accordance with an embodiment of the invention is shown in FIG. 2. The graph 200 depicts operational complexity along the x-axis and computation complexity along the y-axis. Typically, computational complexity can indicate the total computation workload, but not necessarily the actual hardware complexity. As hardware design also includes memory and control units, the complexity of hardware implementations can also depend on the diversity of operation and the data flow patterns (these factors are referred as operational complexity). The main operation in the AS 202 and EU 204 tasks is the inner product operation, which has low operational complexity. To the contrary, the LS 206 task involves matrix factorization, which typically requires a variety of basic operations in series with complex data flow, thereby having high operational complexity. The graph further illustrates that the AS 202 part of the architecture design has the biggest impact on throughput. Therefore, a sufficient level of parallelization can be applied to reduce the reconstruction time. Further, the LS 206 part of the design can play a pivotal role on area efficiency. Note that any hardware resources dedicated to the LS task will have a very low utilization rate. Consequently, designing an LS block exclusively can deteriorate the overall area efficiency, especially when it is parallelized and occupies large areas. Thus, resource sharing should be considered to maximize the hardware utilization.

Although specific graphs illustrating complexity analysis of OMP are discussed above with respect to FIG. 2, any of a variety of techniques for performing complexity analysis of OMP as appropriate to the requirements of a specific application can be utilized in accordance with embodiments of the invention. Techniques for OMP process reformulation toward resource sharing in accordance with embodiments of the invention are discussed further below.

TABLE II

OMP PROCESS COMPUTATIONS AT ITERATION t

| Task | FLOPs* |
|---|---|
| AS | 2nm |
| LS† | 2mt + 3t² |
| EU | 2mt |

*Only the dominant factors are shown.
†Based on incremental Cholesky factorization.

C. OMP Process Reformulation Toward Resource Sharing

In order to enable resource sharing for LS tasks, the following process reformulation techniques can be applied to simplify LS computations in accordance with embodiments of the invention.

Square-Root-Free OMP

There are two steps in the OMP process that can utilize square root operations. Specifically, at iteration t, t square root operations are utilized in the LS task (Table I, Step 3), and a single one is involved in computing the stopping criterion (Table I, Step 5). An explicit implementation of the non-linear operation is not cost-effective, as it cannot be reused by the AS task and will have a very low utilization rate. Therefore, in various embodiments, the square root operations can be eliminated through reformulation of the process.

A solution to the LS problem in (9) can be computed by solving the normal equation given by $$\Phi x(\Lambda) = A_\Lambda^T y. \tag{10}$$

where $\Phi = A_\Lambda^T A_\Lambda \in \mathbb{R}^{k \times k}$ is a positive-definite matrix. By using Cholesky factorization, $\Phi$ can be decomposed as $$\Phi = L'L'^T, \tag{11}$$

where $L' \in \mathbb{R}^{k \times k}$ is a lower-triangular matrix. Note that square root operations are involved in computing the diagonal elements of L' in the conventional Cholesky factorization method. To avoid this, an alternative Cholesky factorization method can be adopted, which essentially eliminates square root operations by taking out the square-rooted factors from both L' and $L'^T$ as $$\Phi = (L'D'^{-1})(D'D')(D'^{-1}L'^T) = LDL^T, \tag{12}$$

where $D' \in \mathbb{R}^{k \times k}$ is a diagonal matrix that contains all the square-rooted factors and satisfies diag(D')=diag(L'), $L=L'D'^{-1} \in \mathbb{R}^{k \times k}$ is a lower-triangular matrix whose diagonal elements are all ones, and $D=D'^2 \in \mathbb{R}^{k \times k}$ is a diagonal matrix that is free of square roots. By substituting $\Phi$ with (12), the normal equation in (10) becomes $$LDL^T x(\Lambda) = A_\Lambda^T y. \tag{13}$$

Equation (13) can be solved through a series of vector operations. First, matrix-vector multiplications are utilized to compute $$u = A_\Lambda^T y. \tag{14}$$

Then, forward substitution (FS) is needed for solving v from $$Lv=u. \quad (15)$$

As D is a diagonal matrix, divisions are involved in computing $$w=D^{-1}v. \quad (16)$$

Lastly, backward substitution (BS) is utilized for computing x(Λ) from $$L^T x(\Lambda)=w. \quad (17)$$

Note that all these operations can be supported by the computation cores through different configurations as discussed further below.

The stopping criterion $\|r_t\|_2 \leq \varepsilon$ can be reformulated as $r_t^T r_t \leq \varepsilon^2$ and computed with doubled dynamic range. Since the floating-point data format is used in many embodiments, dynamic range is no longer a liming factor. Therefore, the OMP process can be free of square root units after the reformulation.

Incremental Cholesky Factorization

In each iteration of OMP, only a single atom may be added to the active set. More specifically, at iteration t $$\Lambda_t = \Lambda_{t-1} \cup \varphi, \quad (18)$$

and $$A_{\Lambda_t} = [A_{\Lambda_{t-1}} \, a_\varphi], \quad (19)$$

where φ is the index of the new active atom. According to (19), the square matrix $\Phi_t = A_{\Lambda_t}^T A_{\Lambda_t} \in \mathbb{R}^{t \times t}$ in (10) can be partitioned as $$\Phi_t = \begin{bmatrix} \Phi_{t-1} & A_{\Lambda_{t-1}}^T a_\varphi \\ a_\varphi^T A_{\Lambda_{t-1}} & a_\varphi^T a_\varphi \end{bmatrix}, \quad (20)$$

where $\Phi_{t-1} = A_{\Lambda_{t-1}}^T A_{\Lambda_{t-1}} \in \mathbb{R}^{t-1 \times t-1}$, $A_{\Lambda_{t-1}}^T \in \mathbb{R}^{t-1}$ is a column vector, and $a_\varphi^T a_\varphi$ is a scalar. Note that (20) indicates at iteration t, the $\Phi_t$ in the LS problem can be constructed from $\Phi_{t-1}$ by adding only a new row or column. In correspondence to (20), the Cholesky factorization matrices in (12) hold the same property, which leads to $$L_t D_t L_t^T = \begin{bmatrix} L_{t-1} & \vec{0} \\ l_{21}^T & 1 \end{bmatrix} \begin{bmatrix} D_{t-1} & \vec{0} \\ \vec{0}^T & d_{22} \end{bmatrix} \begin{bmatrix} L_{t-1} & \vec{0} \\ l_{21}^T & 1 \end{bmatrix}^T, \quad (21)$$

where $l_{21} \in \mathbb{R}^{t-1}$ is a column vector and $d_{22}$ is a scalar. By expanding the equation $\Phi_t = L_t D_t L_t^T$ according to (20) and (21), the following can be derived $$L_{t-1} D_{t-1} l_{21} = A_{\Lambda_{t-1}}^T a_\varphi, \quad (22)$$

and $$d_{22} = a_\varphi^T a_\varphi - l_{21}^T D_{t-1} l_{21}, \quad (23)$$

respectively. Note that $l_{21}$ can be computed using the same method as (13) through a series of matrix-vector multiplication, FS and divisions. Equations (20) and (21) imply that the Cholesky factorization in OMP can be computed in an incremental fashion: in iteration t, the new elements of the factorization matrices (associated with the newly added active atom) can be computed based upon the factorization matrices from iteration t−1. Therefore, in various embodiments, the Cholesky factorization matrices can be stored in dedicated data-path memories, and updated incrementally by computing (22) and (23) only in each iteration. This not only can significantly reduce the computational complexity of the LS task, but can also simplify the operational complexity in terms of control and data access.

Incremental Estimation Update

At iteration t of the original OMP process, a new estimation $x_t$ can be made by solving (10), and the residual $r_t$ is updated as $$r_t = y - A_{\Lambda_t} x_t(\Lambda_t), \quad (24)$$

According to (10) and (24), $$A_{\Lambda_t}^T r_t = A_{\Lambda_t}^T y - A_{\Lambda_t}^T A_{\Lambda_t} x_t(\Lambda_t) = \vec{0}. \quad (25)$$

Equation (25) indicates that the updated residual $r_t$ is orthogonal to the current active atoms $A_{\Lambda_t}$ in OMP. In many embodiments, this property can further simplify the LS task. By substituting y in (10) with $r_{t-1} + A_{\Lambda_{t-1}} x_{t-1}(\Lambda_{t-1})$ according to the (24) of iteration t−1, an incremental estimation update method can be derived as the following two steps. First, the updating direction d can be computed by solving the new normal equation $$\Phi_t d(\Lambda_t) = c(\Lambda_t), \quad (26)$$

where $c(\Lambda_t) = A_{\Lambda_t}^T r_{t-1} \in \mathbb{R}^t$. Second, $r_t$ and $x_t$ can be updated based upon previous values and d, as $$r_t = r_{t-1} - A_{\Lambda_t} d(\Lambda_t), \quad (27)$$

and $$x_t = x_{t-1} + d, \quad (28)$$

respectively. Note that $c(\Lambda_t)$ is part of the correlation coefficients that have been computed in the AS task. Furthermore, from (19) and the (25) of iteration t−1, it can be derived $$c(\Lambda_t) = \begin{bmatrix} A_{\Lambda_{t-1}}^T r_{t-1} \\ a_\varphi r_{t-1} \end{bmatrix} = \begin{bmatrix} \vec{0} \\ a_\varphi r_{t-1} \end{bmatrix}. \quad (29)$$

Equation (29) indicates that $c(\Lambda_t)$ is a 1-sparse vector that has only one non-zero value. Consequently, the matrix-vector multiplications in (14) and the subsequent FS and divisions in (15) and (16) can be completely bypassed.

Overall, applying the reformulation techniques not only reduces the computational complexity of the LS task from $O(mk^3)$ to $O(mk^2)$ but can also simplify its operational complexity in terms of data flow control and scheduling. Specifically, after the reformulation, the LS task in each iteration only involves a few inner products and a single FS for updating the Cholesky factorization matrices as shown in (22) and (23), and a single BS for computing the updating direction as shown in (17). This greatly facilitates the resource sharing in the architecture design. VLSI architectures for CS reconstruction in accordance with embodiments of the invention are discussed further below.

Architecture Design

In order to achieve real-time and energy efficiency, a highly parallel and scalable VLSI architecture with configurable PEs can be utilized. In many embodiments, the computing resources for performing the AS task are reused by the LS and EU tasks. As a result CS reconstruction engines in accordance with many embodiments of the invention feature a high utilization rate of the computing resources and high area efficiency. VLSI architectures utilizing various computation cores and data-path memories in accordance with embodiments of the invention are discussed further below.

A. Computation Cores

Figure 3:
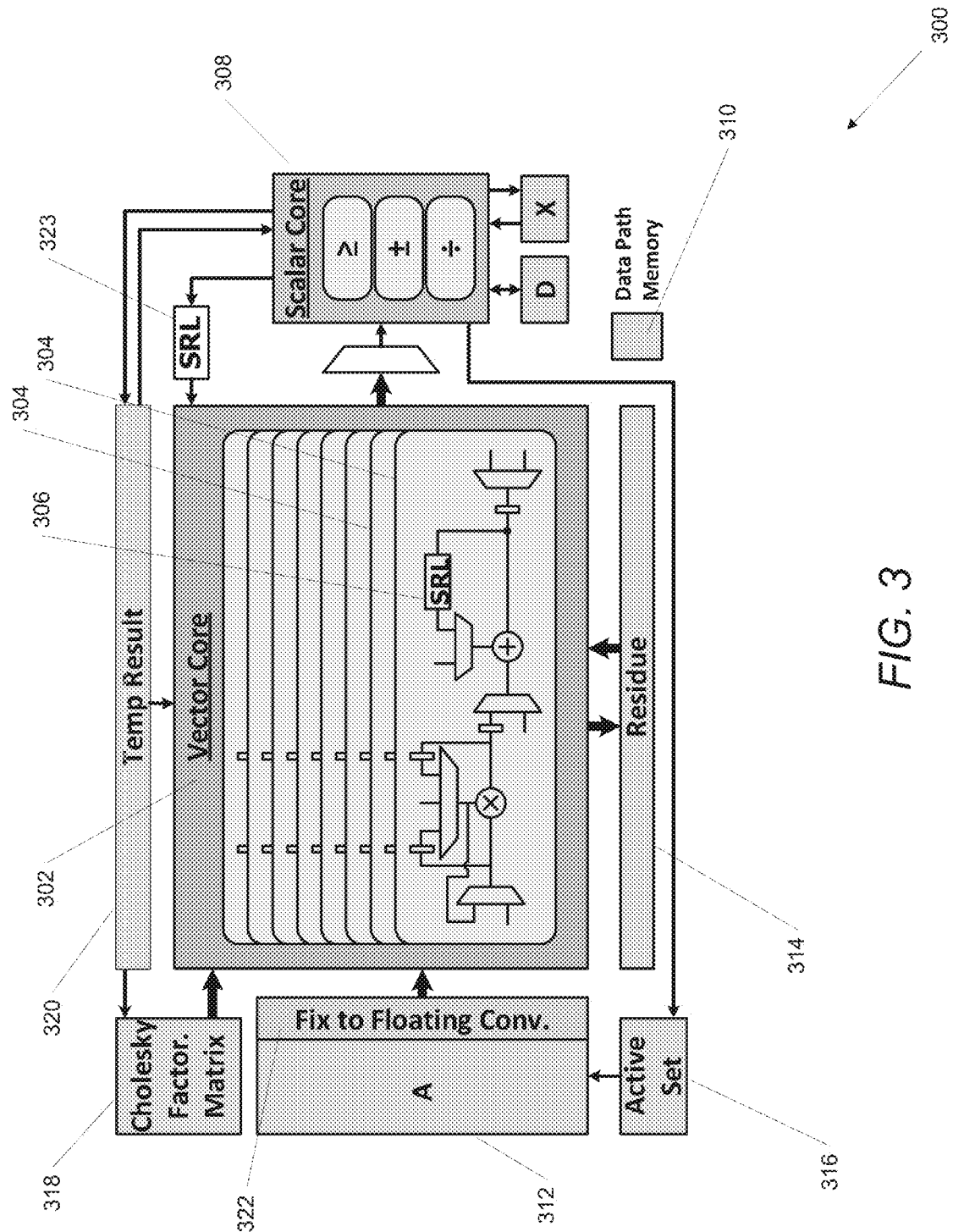
FIG. 3 is a block diagram of a VLSI architecture of a CS reconstruction engine in accordance with an embodiment of the invention.

A top-level block diagram of a VLSI architecture of a CS reconstruction engine in accordance with an embodiment of the invention is shown in FIG. 3. The VLSI architecture 300 includes a vector core 302 that integrates multiple PEs 304 in parallel with a flexible data-path as further discussed below. Both the PEs 304 and the various data-path connections can be dynamically configured through microcode. This can enable the vector core to support a selective set of vector operations including element-wise addition, multiplication, accumulation, and multiply-accumulation (MAC), as well as vector-scalar product and inner product. A shift register logic (SRL) unit 306 that provides optional latency can be used in the feedback path of each PE for enabling the folding capability to process long vectors. In many embodiments, the VLSI architecture 300 also includes a scalar core 308 that integrates a comparator, a sequential divider and two adders with the configurable data-path. In several embodiments, the scalar core 308 can support scalar comparison, addition, accumulation, and division. Depending on the top-level data-path configuration, the scalar core 308 can either post-process a selective result from the vector core 302 (e.g. an inner product) or process independent data in parallel. When the two cores 302 and 308 are cascaded as a processing group, more advanced operations, such as correlation sorting, folded inner product, FS, and BS, can be executed. Another SRL unit 323 is also used in the feedback path between the vector and scalar core to enable the folding capability for computing large size FS and BS.

B. Data-Path Memories

In various embodiments, the vector 302 and the scalar core 308 are linked by data-path memories 310. The complex data flow of OMP is enforced by customized local memory controllers, which are synchronized by a top-level finite-state machine (FSM). In many embodiments, most data-path memories are implemented using RAM macros. This helps improve power efficiency especially when the supported problem size is large, since most of the data ordering or shuffling can be realized by processing its pointers instead.

For the CS reconstruction of different bio-medical signals, the sampling matrix $A=\Theta\Psi\in\mathbb{R}^{m\times n}$ is often different due to the variety in sparse domain $\Psi$. However, A serves as fixed coefficients and need not to be updated during the operations. In various embodiments, A is explicitly stored in the largest data-path memory 312 in order to accommodate the CS reconstruction on different bases. Note that all the elements in A can be fully accessed during the AS task in every iteration. This may lead to a high memory access intensity. Specifically, data may need to be accessed once per two FLOPs on average. Consequently, the memory bandwidth B utilized by the vector core 302 for parallel processing can be characterized as $$B = f_{PE} \cdot \frac{N_{PE}}{2} \cdot W \cdot p, \quad (30)$$

where $f_{PE}$ is the operating frequency of PEs, $N_{PE}$ is the number of FLOPs performed by a single PE in each clock cycle ($N_{PE}=2$ in our case), W is the data word-length, and p is the parallelism (i.e. number of PEs) of the vector core.

Note that the system throughput will become memory-bounded if the right-hand side (RHS) of (30) is greater than the left-hand side (LHS). In this case, further increasing $f_{PE}$ or p likely will not boost the throughput but only degrade the power and area efficiency of the design. On the other hand, when the LHS of (30) is greater, the available memory bandwidth in the system is not fully utilized. Further speedup can be achieved through more parallelization of PEs 304 or more pipelining if applicable. In several embodiments, the abundant block RAM (BRAM) resources on the FPGA device are utilized to provide a balanced system performance for parallel processing where the on-chip memory bandwidth is matched with the throughput of the vector core 304 according to (30).

Different from A, all the other variables in the OMP process may need to be updated in every iteration. In iteration t, the residual $r_t\in\mathbb{R}^{m\times 1}$, the active set $\Lambda_t\in\mathbb{R}^{k\times 1}$, the estimation $x_t\in\mathbb{R}^{k\times 1}$ (see Table I), and the Cholesky factorization matrices are updated based upon their values from iteration t−1. Consequently, these variables cannot share the same memory space through time-multiplexing as they all have to be stored at the end of each iteration. In many embodiments, dedicated data-path memories are assigned to each of these variables. In the illustrated embodiments, the residual is stored in memory 314, the active set is stored in memory 316, and the Cholesky factorization matrices are stored in path memory 318. In contrast, the rest of the variables in OMP are all temporary. In order to maximize the memory utilization, they are buffered as temporary results in a shared memory 320 through time-multiplexing. Further, a parallelized fixed-point to floating-point conversion interface 322 can be utilized in order to bridge the floating-point vector core and the fixed point A memory as further discussed below.

Although specific VLSI architectures of a CS reconstruction engine are discussed above with respect to FIG. 3, any of a variety of VLSI architectures utilizing various computation cores and data-path memories for a reconstruction engine as appropriate to the requirements of a specific application can be utilized in accordance with embodiments of the invention. Data formats for use in reconstruction engines in accordance with embodiments of the invention are discussed further below.

C. Data Format

In many embodiments, the dynamic range requirements of each computing unit can be investigated based upon statistic information extracted from double-precision MATLAB simulations. In various embodiments, the optimal data format can be determined to preserve software-level accuracy for recovering a wide range of bio-medical signals. In various simulations, the input signals of different problems (i.e. biomedical signals) can be emulated by randomly generating their sparse coefficients on a selective orthogonal basis. These can include (but are not limited to) canonical basis, discrete wavelet transform (DWT) basis, and/or discrete cosine transform (DCT) basis. Note that the sparse coefficients can also be scaled such that they follow the power-law decay. The generated signals are often sampled by Bernoulli random matrices and contaminated by additive Gaussian noise. Then, the dynamic range statistics in each step of the OMP process can be extracted from the subsequent signal reconstruction. Note that the emulation method used in various embodiments, are a first-order approach for estimating the dynamic range requirement for a wide range of bio-medical signals. To determine the optimized word-length for a specific signal type, using more representative signal samples as the simulation input can be preferred.

Figure 4:
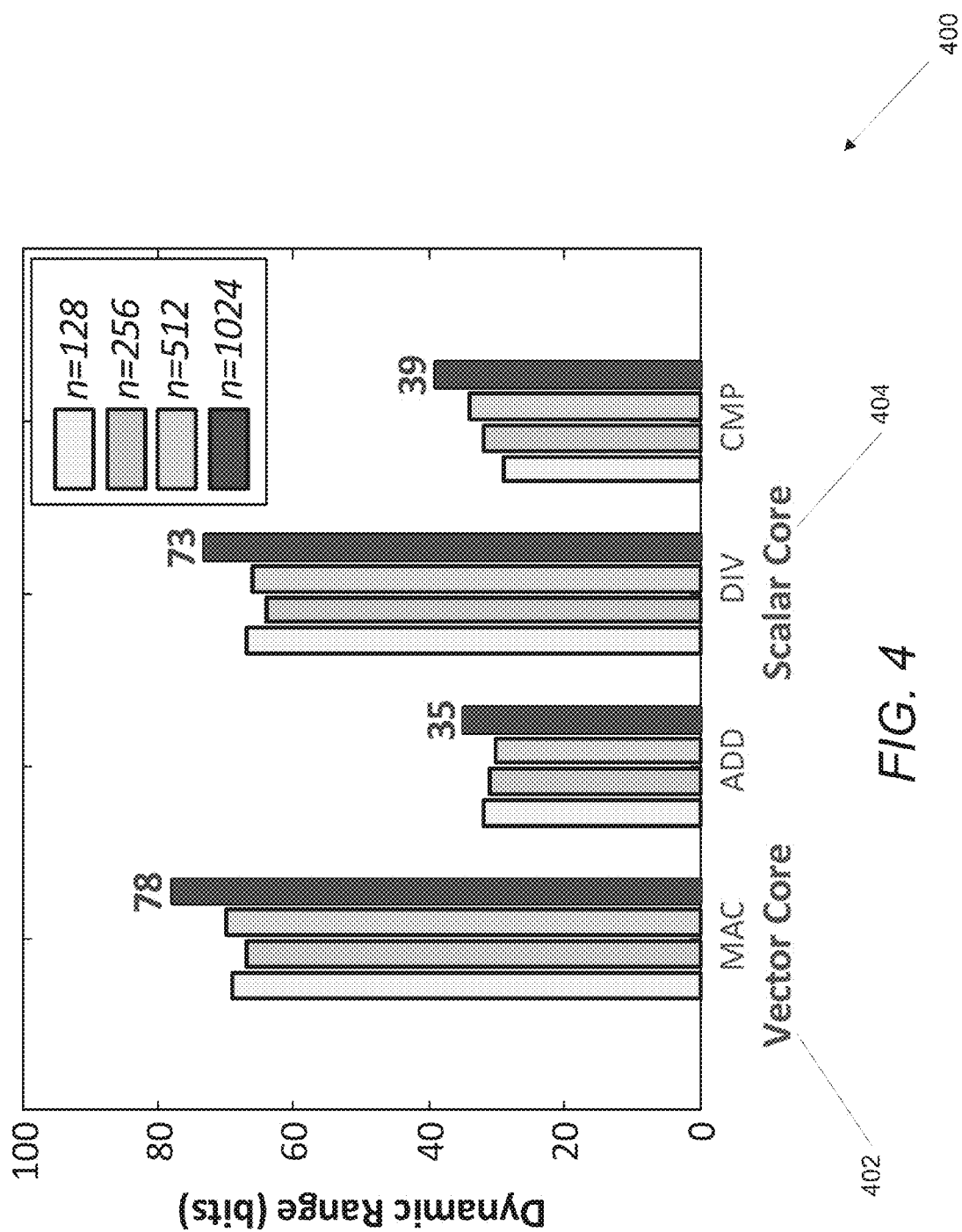
FIG. 4 is a chart illustrating worst-case dynamic ranges of hardware units of a CS reconstruction engine in accordance with an embodiment of the invention.

A chart illustrating a worst-case dynamic range for hardware units (i.e. vector and scalar cores) for preserving software-level accuracy in accordance with an embodiment of the invention is shown in FIG. 4. The chart 400 illustrates that when a fixed-point data format is used, the word-length typically utilized by the MAC unit in the vector core 402 is 78 bits and the adder, divider, and comparator unit in the scalar core 404 is 35, 73, and 39 bits, respectively. Such a large dynamic range is largely due to the solution searching characteristic of OMP: the scales of most variables are gradually scaled down as the residual approaches zero. In various embodiments, sharing the computing resources in different tasks can also increase the dynamic range requirement. This is because the dynamic range of a hardware unit has to cover the worst case of all the different tasks. The results illustrated in FIG. 4 indicate that a fixed-point implementation typically requires impractical data word-length and large area overhead in order to fulfill the accuracy target. Alternatively, the single-precision floating-point data format is able to provide the adequate dynamic ranges with a fixed 32-bit word-length. The reduced data word-length can lead to significant area reduction, primarily from the data-path memories. Therefore, the single-precision floating-point data format can be more suitable for various targeted applications.

Nonetheless, A is stored in a fixed-point data format in many embodiments. Note that A serves as fixed coefficients and is updated during the operations in the same problem. Therefore, it can have a limited dynamic range. As shown in FIG. 3, a parallelized fixed-point to floating-point conversion interface 322 can be inserted in order to bridge the floating-point vector core and the fixed point A memory.

Although a chart illustrating worst-case dynamic ranges for hardware units to preserve software-level accuracy are discussed above with respect to FIG. 4, any of a variety of worst-case dynamic ranges for hardware units to preserve software-level accuracy as appropriate to the requirements of a specific application can be utilized in accordance with embodiments of the invention. Dynamic configuration of various VLSI architectures in accordance with embodiments of the invention are discussed further below.

D. Architecture Dynamic Configuration

In many embodiments, the same computation cores of the VLSI architecture can be time-multiplexed (via dynamic configuration) to perform the three tasks of OMP. Due to the intrinsic data-dependency between different tasks, this resource sharing technique introduces little overhead in throughput but improves the hardware utilization rate, allowing for more PEs to be mapped onto the FPGA for further speed-up.

Figure 5A:
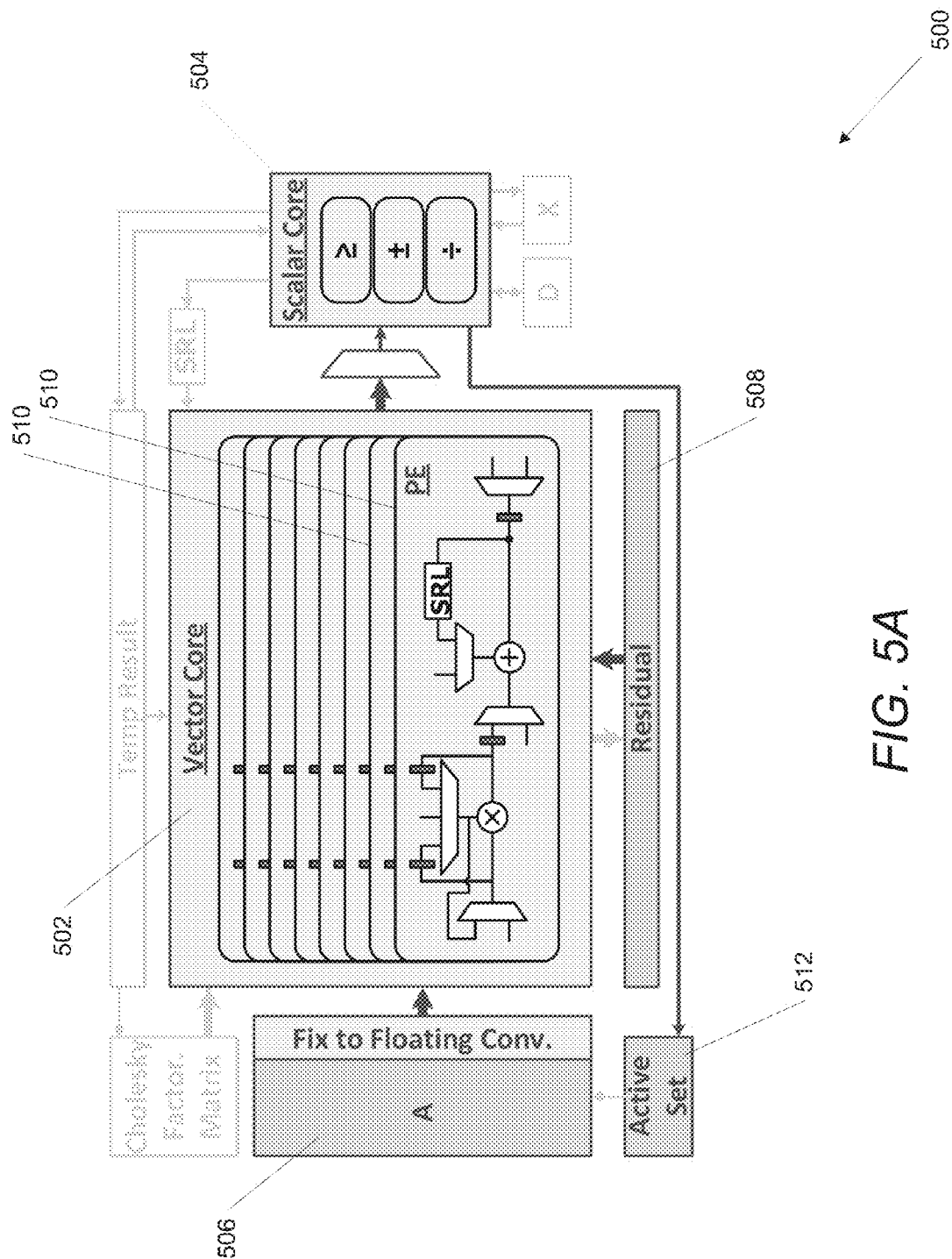
FIG. 5A is a block diagram of a dynamic configuration of a VLSI architecture in performing an atom searching (AS) task in accordance with an embodiment of the invention.
Figure 5B:
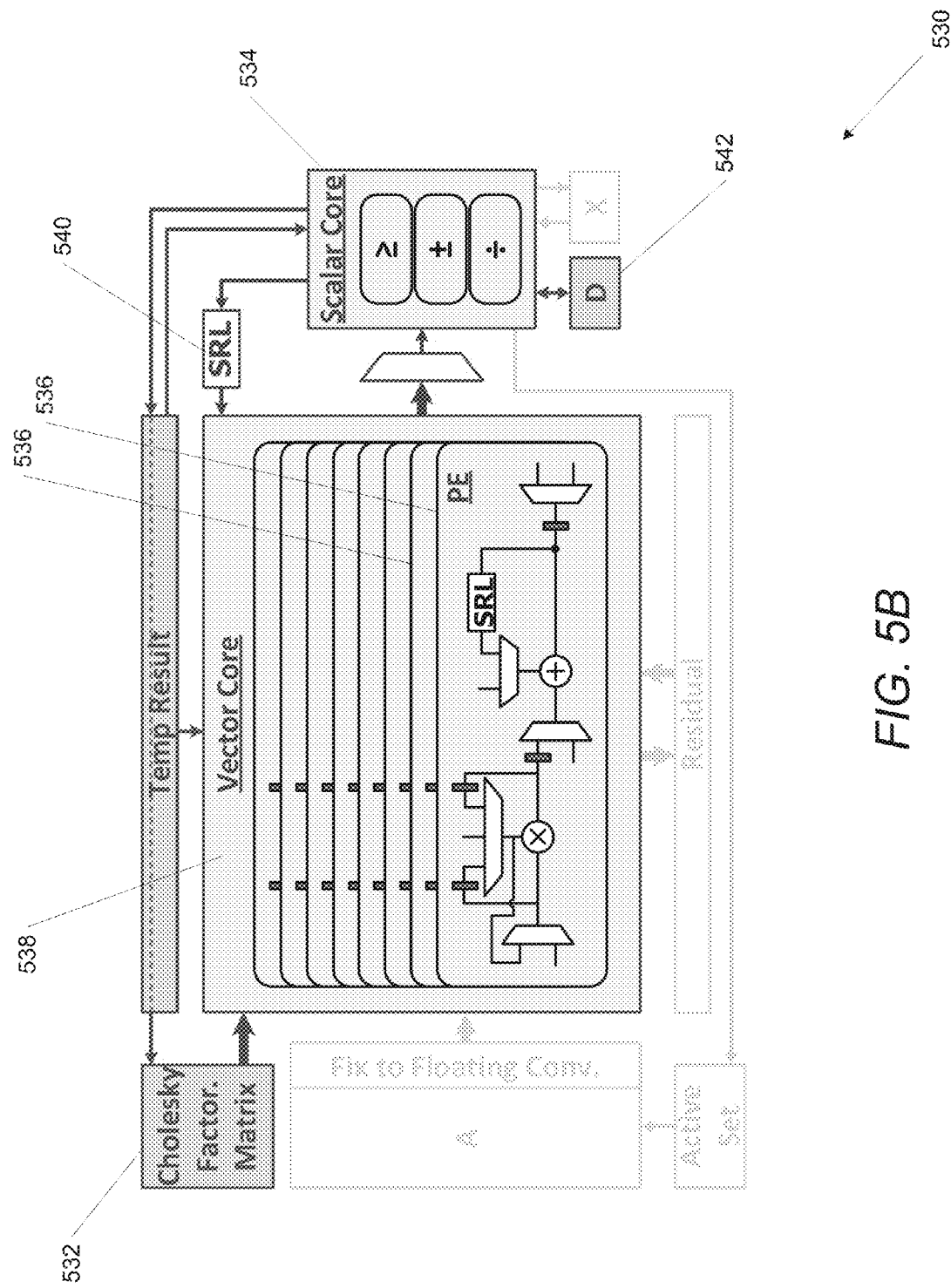
FIG. 5B is a block diagram of a dynamic configuration of a VLSI architecture in performing a least squares (LS) task in accordance with an embodiment of the invention.
Figure 5C:
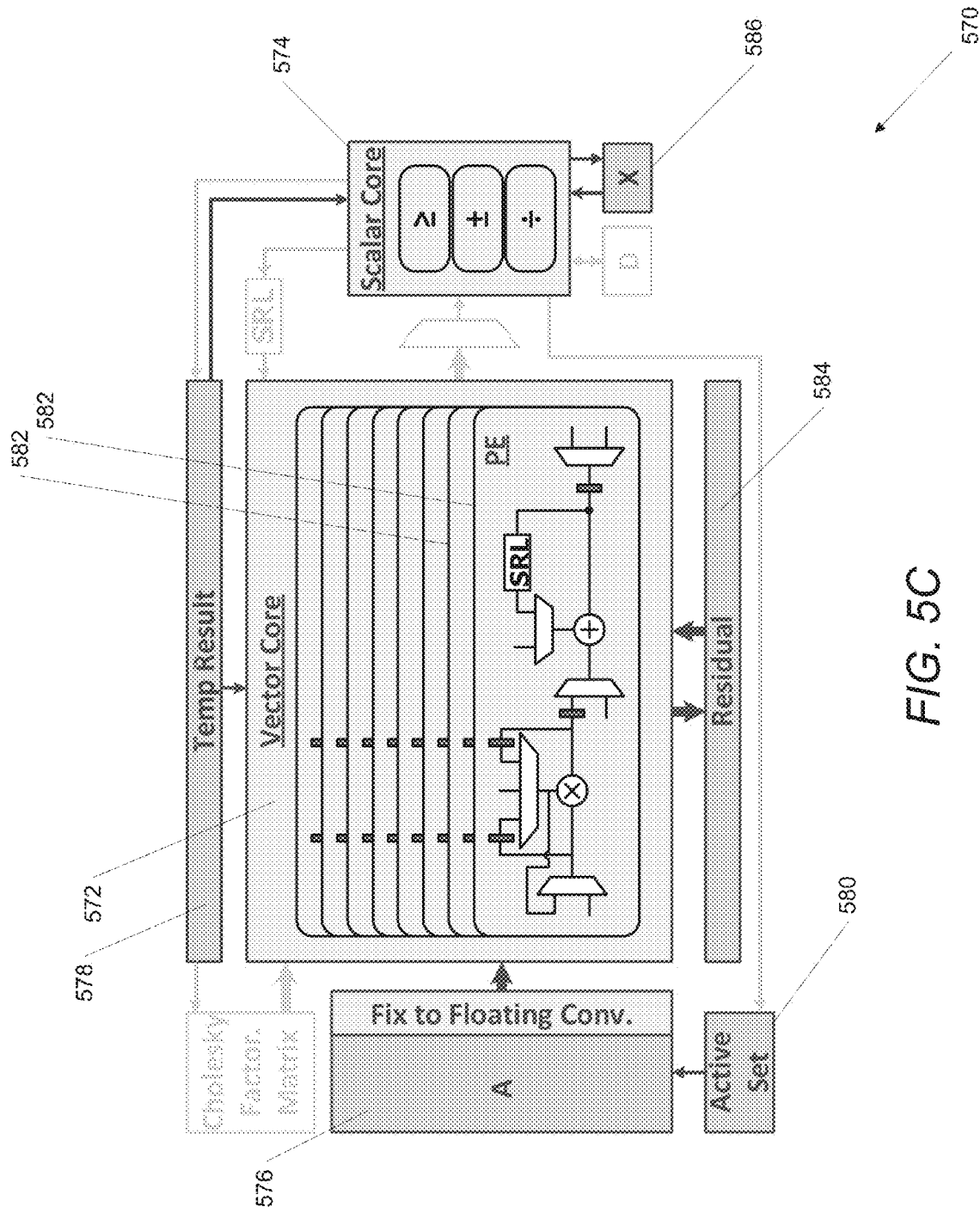
FIG. 5C is a block diagram of a dynamic configuration of a VLSI architecture in performing an estimation update (EU) task in accordance with an embodiment of the invention.

Block diagrams illustrating dynamic configuration of a VLSI architecture for performing various tasks of OMP in accordance with an embodiment of the invention is shown in FIGS. 5A-C. A first configuration 500 of the VLSI architecture of a CS reconstruction engine in accordance with an embodiment of the invention is illustrated in FIG. 5A can be utilized in performing the AS task. In many embodiments, a vector core 502 is cascaded with a scalar core 504 in a pipeline. The vector core 502 accesses $a_i$ and $r_{t-1}$ in parallel from A and the residual memories 506 and 508, respectively. In several embodiments, PEs 510 are configured to compute their inner product as $c(i)=a_i^T r_{t-1}$. The scalar core 504 accumulates the result when folding is enabled and compares the absolute values of $c(i)$ with that of $c(i-1)$. The smaller value is dropped, while the bigger value and the associated column index is buffered for the next comparison. After all the correlation coefficients are compared, the column index of the maximum component is written into the active set memory 512.

A second configuration 530 of the CS reconstruction engine is illustrated in FIG. 5B can be utilized in performing the LS task. In various embodiments, a series of matrix-vector multiplications, divisions, FS, and/or BS are executed for updating the Cholesky factorization matrices as in (22) and (23) and solving the normal equation as in (17). The Cholesky factorization matrices can be stored in data-path memory 532. For computing matrix-vector multiplications, a similar configuration to that for the AS task can be used. However, in order to support FS and BS using iterative vector operations, a global feedback path can be enabled to link the adder in scalar core 534 to the PEs 536 in the vector core 538 into parallel loops. A SRL unit 540 is also used in the feedback path to enable the folding capability for computing large size FS and BS. Note that performing FS and BS iteratively has little impact on the overall throughput. This is because the LS task is typically not a throughput bottleneck. But, it allows for reusing the vector core 538 for computation and improves the hardware utilization. In addition, when the FS in (22) is executed iteratively using the second configuration 530 of the CS reconstruction engine, the divisions can be scheduled to the scalar core 534 and executed by the sequential divider in the pipeline and stored in memory 542.

A third configuration 570 of the CS reconstruction engine is illustrated in FIG. 5C can be utilized in performing the EU task. In many embodiments, the vector core 572 and the scalar core 574 are configured to update the estimation results separately. The vector core 572 accesses $A_{\Lambda_t}$ and $d(\Lambda_t)$ from A memory 576 and the temporary result memory 578, respectively. Note that the active atoms of A can be accessed by using the contents from the active set memory 580 as the read address. In many embodiments, the PEs 582 can be configured to compute $v=A_{\Lambda_t}d(\Lambda_t)$ column-wise using vector-scalar multiplication and element-wise MAC. Once the result v is available, the residual $r_t$ is updated by the vector core 572 in parallel as $r_t=r_{t-1}+v$ and saved in a residual memory 584. In the meanwhile, the scalar core 574 updates $x_t$ in series as $x_t(i)=x_{t-1}(i)+d(i)$ whenever $d(i)$ is read out from the temporary memory 578, where $x_t$ is stored in memory 586. Although specific VLSI architecture configurations are discussed above with respect to FIGS. 5A-C, any of a variety of VLSI architecture configurations can be utilized by a CS reconstruction engine as appropriate to the requirements of a specific application can be utilized in accordance with embodiments of the invention. VLSI architecture scalability considerations in accordance with embodiments of the invention are further discussed below.

E. Architecture Scalability and Flexibility

In many embodiments, the proposed architecture can be parameterized and features scalability. Table III (reproduced below) summarizes various user-defined parameters supported in many embodiments of the invention. For circuit level optimization, the user can specify a word-length and the pipeline stages of each arithmetic unit to meet different precision and performance requirements. In addition, the user can also tune the memory size and the parallelism of PEs through architecture parameters for accommodating different problem size and throughput specifications.

Since the data-path memories are separated from the computation cores, the scaling of one part has little dependency on the other given that the timing difference in control signals can be handled by adjusting the FSM in local controllers. By adjusting the size of data-path memories coherently, this architecture can be scaled to accommodate different problem settings (n, m, k). Note that the computing throughput of the vector core can be configured to remain the same if the parameters in (30) are unchanged. However, the system throughput may be different due to the change in total computational complexity. When implemented on reconfigurable platforms, such as FPGAs, the maximum problem size and sparse coefficient capacity supported by the architecture can be limited by the amount of BRAM resources available. To support even larger problems, off-chip memories can be integrated with the FPGA device through high-speed input/outputs (I/Os). In this case, the I/O bandwidth usually becomes the bottleneck of system throughput.

TABLE III

USER-DEFINED PARAMETERS IN THE VLSI ARCHITECTURE

| | Parameter | Description |
|---|---|---|
| Circuit | $\{W_M, W_E\}$ | Word-length of mantissa, exponent |
| | $\{S_A, S_M, S_D, S_C\}$ | Pipeline stages of adder, multiplier, divider, comparator |
| Architecture | P | Parallelism of PEs in VC |
| | N | Signal Dimension n |
| | M | Measurement Dimension m |
| | K | Signal Sparisty Level k |

As discussed above, the proposed design provides a user with flexibility to accommodate different problem sizes, signal sparsity levels, and flow controls on the reconstruction process through user-defined architectural parameters at the time of compiling and with static control signals that can be specified during operation. Architectural parameters that can be defined during compiling include:

n: the number of columns of the sampling matrix A, aka, the signal dimension, the number of atoms in the selective dictionary for signal reconstruction;

m: the number of rows of the sampling matrix A, aka, the measurement dimension, the number of measurements, the dimension of the dictionary atoms for signal reconstruction;

k: the signal sparsity level on a selective basis, aka, the number of sparse coefficients to be reconstructed;

p: the parallelism of the vector core, aka, the number of PEs in the vector core; and $W=[w_1, w_2, \ldots, w_l]$: the word-length of the arithmetic units, including multiplier, adder, comparator, and divider. Note that when floating point data format is used, l=2, and $w_1$ is the number of mantissa bits, $w_2$ is the number of exponent bits.

In several embodiments, n, m, k determine the maximum problem size that a VLSI circuit can process and the size of data-path memories and control units are affected accordingly. In some embodiments, p can determine the amount of computing resources deployed in a vector core for parallel computing, which can allow the user to trade-off performance with area and power consumption, where the control units are affected accordingly.

In various embodiments, static controls signals that can be specified during operation include:

problem_n: the actual n of the current problem (problem_n≤n);

problem_m: the actual m of the current problem (problem_m≤m);

problem_k: the actual k of the current problem (problem_k≤k) (sets the maximum number of iterations of the reconstruction process); and epsilon: the reconstruction error bound of the stopping criterion (it affects the number of sparse coefficients to be reconstructed, the number of iterations of the reconstruction process (reconstruction time), and the reconstruction error).

Although specific scalability and flexibility considerations related to VLSI architectures for CS reconstruction engines are discussed above, any of variety of scalability and flexibility considerations as appropriate to the requirements of a specific application can be utilized in accordance with embodiments of the invention. Hardware implementation and experimental results of VLSI architectures of CS reconstruction engines in accordance with embodiments of the invention are discussed further below.

Hardware Implementation and Experimental Results

A. Testing Environment

In many embodiments, the techniques discussed above regarding VLSI architectures can be utilized to implement a CS reconstruction engine using a Xilinx KC705 evaluation platform. In various embodiments, the evaluation platforms are equipped with a Kintex-7 XC7K325T-FBG900 FPGA (speed grade –2) and a number of off-the-shell components for enhancing the system capabilities in memory, data communication, and/or networking.

Figure 6A:
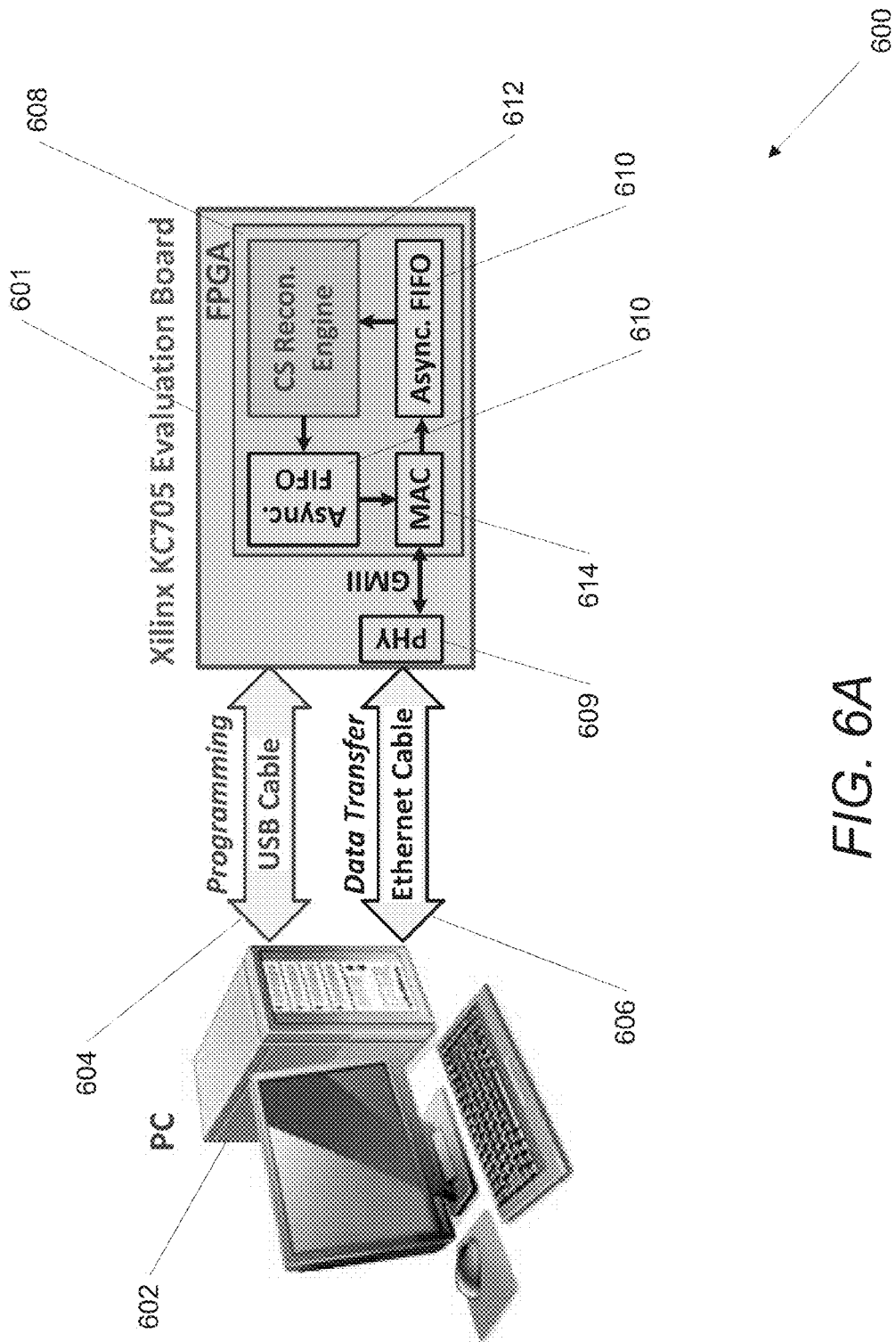
FIGS. 6A-B are evaluation platform setup diagrams in accordance with an embodiment of the invention.

An evaluation platform setup for testing a VLSI reconstruction engine architecture for a CS reconstruction engine in accordance with an embodiment of the invention is illustrated in FIG. 6A. The evaluation platform setup 600 includes an evaluation board 601 that is connected with a PC 602 through both USB 604 and Ethernet 606 cables. The USB connection can be used to program the FPGA 608 and monitor the chip status via the ChipScope toolkit. The Ethernet connection supports high-speed data transfer between the PC 602 and the evaluation platform 601. In order to bridge the reconstruction engine to the Ethernet network, several Xilinx LogiCORE IP blocks are integrated on the FPGA as glue logic. Specifically, a tri-mode Ethernet media access control (TEMAC) module 614 can be instantiated to drive the 10/100/1000 MHz Ethernet PHY device 609 equipped on the board through a Gigabit media independent interface (GMII). In addition, two asynchronous first-in-first-outs (FIFOs) 610 can be used to link the reconstruction engine 612 and the TEMAC module 614 across different clock domains. To deal with the Ethernet frame format, the FIFO controllers can be customized to perform decapsulation and encapsulation for incoming and outgoing data streams, respectively. As a result, a full-duplex data communication channel that has a 1 Gbps data transfer rate can be established between the reconstruction engine and the PC via the Ethernet.

Figure 6B:
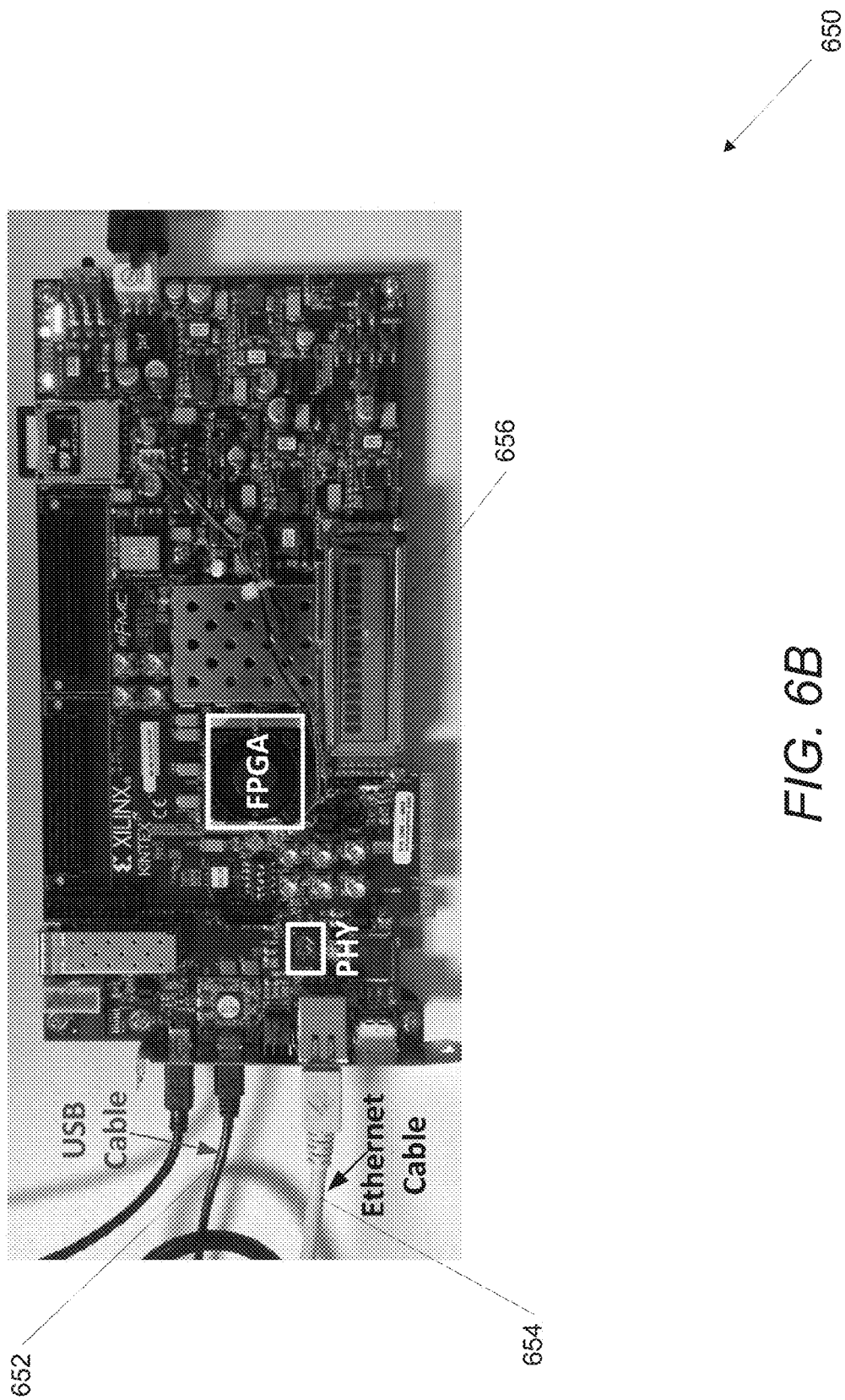

An evaluation platform in accordance with an embodiment of the invention is show in FIG. 6B. The platform 650 can be connected to a PC using both a USB 652 and Ethernet 654 cables as discussed above. In many embodiments, the USB connection can be used to program a FPGA 656 and the Ethernet connection supports data transfer between the PC and the evaluation platform. By utilizing the network infrastructure, the same setup can also be used for remote testing. When the evaluation platform is connected via an Ethernet connection, test vectors can be sent to the reconstruction engine in Ethernet frames from any terminal user belonging to the same local area network (LAN) by specifying the MAC address of the TEMAC as the destination address. Therefore, once the FPGA is programmed using the configuration shown in FIGS. 6A and 6B, the reconstruction engine is typically up online and ready for real-time signal recovery. Although specific implementation and evaluation platforms for VLSI architectures are discussed above with respect to FIGS. 6A-B, any of a variety of implementation and evaluation platforms as appropriate to the requirements of specific applications can be utilized in accordance with embodiments of the invention. Implementation results in accordance with embodiments of the invention are discussed further below.

B. Implementation Results

In many embodiments, circuit and architecture level flexibility can be tested by mapping the results of various parameter settings as discussed below. In several embodiments, the setting that produces maximum performance and resource utilization can be selected for further implementations. In various embodiments, by efficiently utilizing the resources on the FPGA, 128 PEs can be deployed in the vector core, and the reconstruction engine can support a flexible problem size of $n \leq 1740$, $m \leq 640$. In addition, various implementations can support up to $k \leq 320$ sparse coefficients in signal reconstruction. In many embodiments, allowing more coefficients to be reconstructed can add finer details to the recovered signal. This can be critical to achieving the high reconstruction accuracy for wireless healthcare applications, when the signal is not ideally sparse on the selective basis.

Table IV (reproduced below) summarizes various system performances and resource utilization profiles of an FPGA implementation in accordance with an embodiment of the invention. After inserting 6 pipeline stages into the floating-point divider and performing global retiming, the CS reconstruction engine has a balanced data-path delay distribution. In many embodiments, the critical path is found to pass through the floating-point multiplier, which is massively distributed in the vector core. In various embodiments, the whole system can have an operating frequency of 53.7 MHz. The implementation can use 91% of the LUTs, 31% of the DSP48 slices, and 98% of the BRAMs on the FPGA device. In a variety of embodiments, all the BRAMs are used for constructing the data-path memories, where 65% of the usage is dedicated for storing A in a 10-bit fixed-point data format. In each floating-point multiplier, two DSP48 slices can be utilized to further improve the critical path delay. Thus, a total of 256 DSP48 slices can be used in 128 PEs. Note that among the total LUT usage, 90% is contributed by the vector core. This means the proposed architecture has a high area efficiency, which results from the reformulation and resource sharing efforts. As a result, in many embodiments, 90% of the logic resources are utilized to parallelize the PEs for achieving higher processing throughput. Moreover, shared by all the tasks of OMP, the vector core can achieve a nearly 100% utilization rate during the operations. Evaluations of reconstruction accuracy in accordance with embodiments of the invention are discussed further below.

TABLE IV

IMPLEMENTATION RESULTS ON FPGA*

| | System | Usage Breakdown† | | |
|---|---|---|---|---|
| | | VC | SC | DMs |
| Frequency | 53.7 MHz | | | |
| LUTs | 186,799 (91%) | 90% | 3% | 7% |
| DSP48s | 258 (31%) | 99% | 0% | 1% |
| Block RAMs | 435 (98%) | 0% | 0% | 100% |

*Xilinx Kintex-7 XC7K325T-FBG900
†VC: vector core, SC: scalar core, DMs: data-path memories C. Accuracy Benchmarking In order to evaluate the reconstruction accuracy, sample data can be utilized to perform CS sampling and reconstruction. As an illustrative example, ECG data from the MIT-BIH database can be used to perform CS sampling and reconstruction and analyzed for benchmarking. In the experiments, the ECG signals are segmented with a fixed window size of n=1024 and sampled by a Bernoulli random matrix with different compression (m/n) ratios. Recall from CS theory, that the signals can be uniformly sampled without knowing what their sparse domain is. However, such prior knowledge must be provided in the signal reconstruction.

Figure 7A:
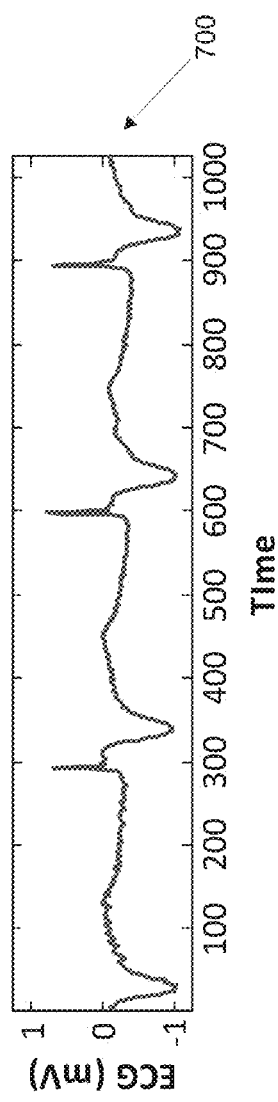
FIGS. 7A-C are graphs illustrating an ECG signal and its associated coefficients in accordance with an embodiment of the invention.
Figure 7B:
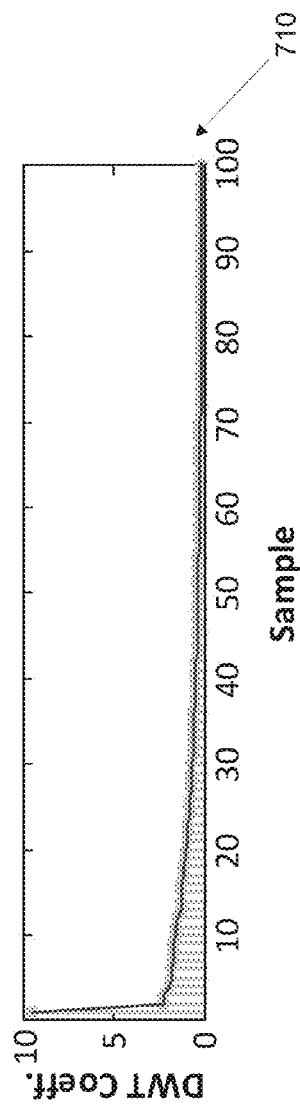
Figure 7C:
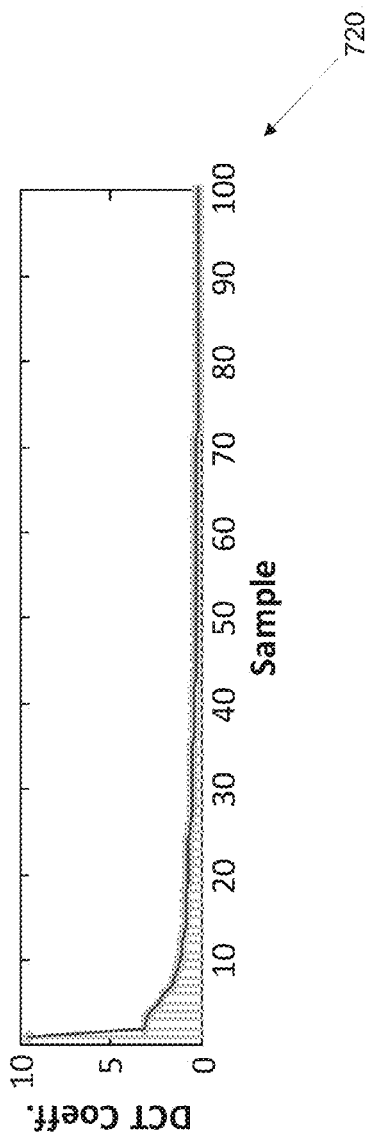

Graphs illustrating an ECG signal and its associated coefficients in accordance with various embodiments of the invention are illustrated in FIGS. 7A-C. The first graph 700 depicts the ECG signal's amplitude in (mV) as a function of time. The second graph 710 in FIG. 7B and third graph 720 in FIG. 7C illustrate the ECG signal's first 100 coefficients on the DWT and DCT basis, respectively. In many embodiments, the coefficients in the DWT and DCT basis follow a power-law delay, and the decay on the DWT basis is slightly faster can the decay on the DCT basis. Typically, the sparsest domain of the signal is highly dependent on the nature of the signal source. Consequently, different signals often exhibit the best sparsity on different basis, and such prior knowledge is usually unavailable in practice.

Graphs illustrating an EEG signal and its associated coefficients in accordance with various embodiments of the invention are illustrated in FIGS. 8A-C. The first graph 800 depicts the EEG signal's amplitude in (μV) as a function of time and is an example EEG signal from the UCSD-EEGLAB database. The second graph 810 in FIG. 8B and third graph 820 in FIG. 8C illustrate the EEG signal's first 100 sorted coefficients on the DWT and DCT basis, respectively. As can be observed from FIGS. 8B-C, the DCT coefficient of the EEG signal is much sparser than its DWT counterpart. Therefore, in order to cover the reconstruction of a wide range of bio-medical signals, it can be beneficial to keep the flexibility of choosing the sampling matrix in hard designs.

For comparison purposes, the ECG signals on the DWT basis using both C program and a reconstruction engine on a FPGA can be reconstructed. The reconstruction accuracy can be measured using a reconstruction SNR (RSNR) defined as $$RSNR = 20 \cdot \log_{10}\left(\frac{\|x\|_2}{\|x - \hat{x}\|_2}\right), \quad (31)$$

where $x \in \mathbb{R}^n$ is the original signal, and $\hat{x} \in \mathbb{R}^n$ is the reconstructed signal. Note that RSNR characterizes the energy ratio of the original signal and the reconstruction error in dB.

Figure 9:
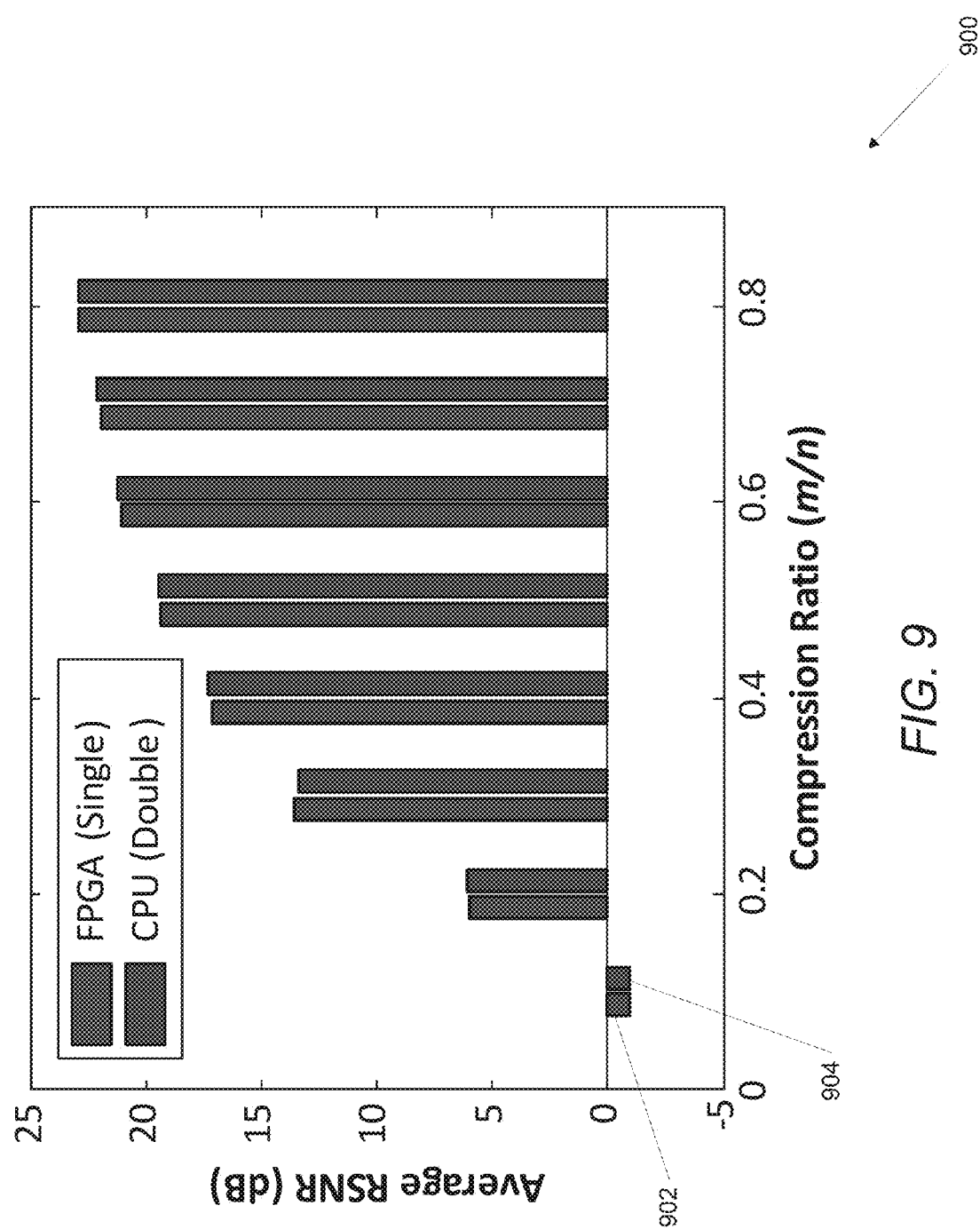
FIG. 9 is a chart depicting average reconstruction signal to noise ratio (RSNR) performance of an ECG signal reconstruction in accordance with an embodiment of the invention.

A chart depicting RSNR performance of an ECG signal on the DWT basis using a reconstruction engine on a FPGA and using compiled C source code in accordance with an embodiment of the invention is shown in FIG. 9. The chart 900 plots the average RSNR (dB) as a function of the compression ratio (m/n). In many embodiments, the average RSNR performance is illustrated as measured from a FPGA reconstruction (single-precision) 902 and C program (double-precision) 904. As a floating-point data format is used, the reconstruction engine on the FPGA is able to achieve the same level of accuracy as the software implementation running on a PC. As the compression ratio increases from 0.2 to 0.3, the RSNR performance is improved by over 2 times. Beyond that, the RSNR gradually saturates to around 23 dB as m increases. On average, a RSNR of 15 dB can be achieved at the compression ratio of 0.3 in the ECG reconstruction test.

Figure 10:
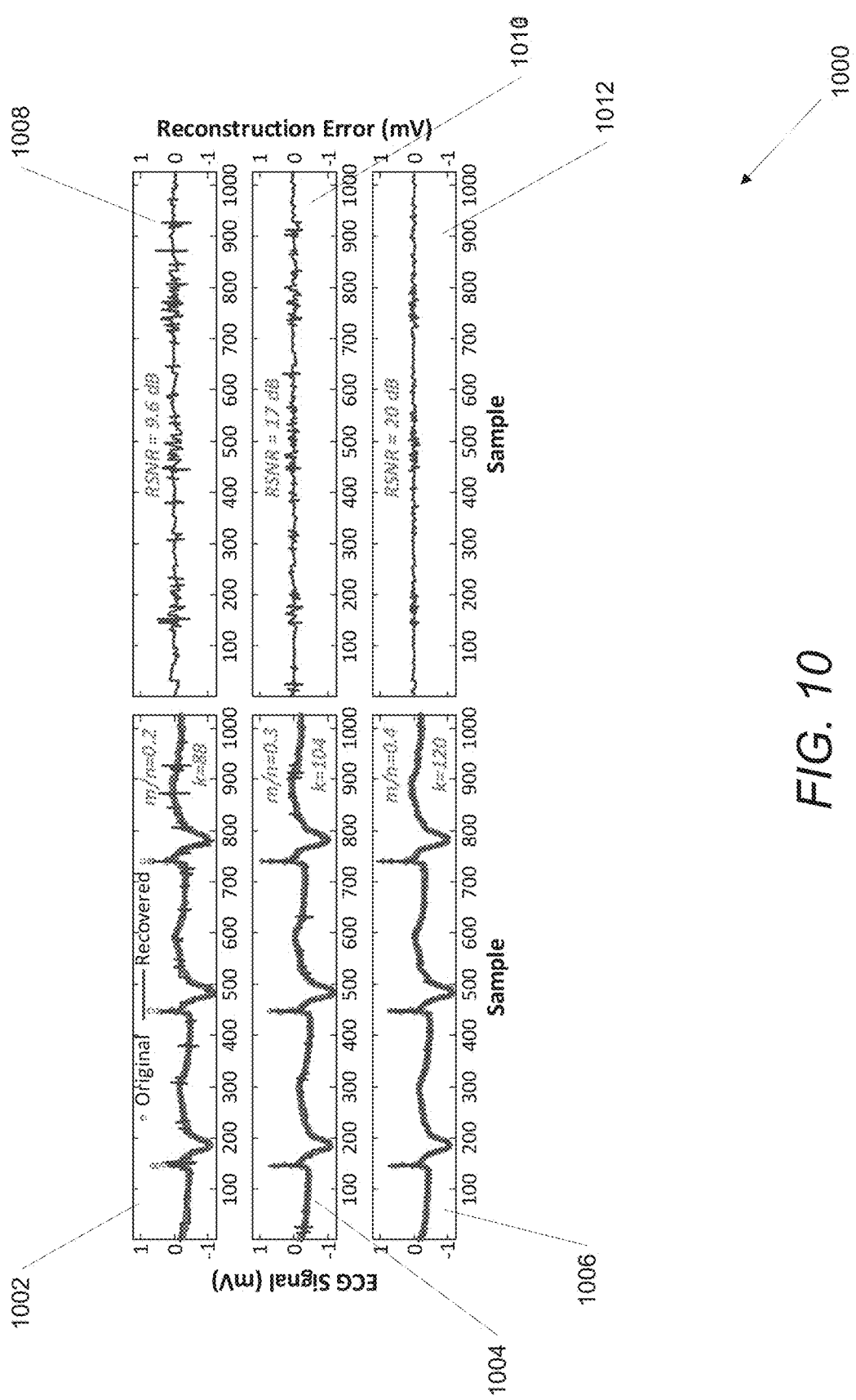
FIG. 10 is a graph illustrating a recovered ECG signals at various compression ratios in accordance with an embodiment of the invention.

Graphs illustrating recovery of an ECG signal at various compression ratios and their corresponding RSNRs are illustrated in FIG. 10. In graphs 1002, 1004, and 1006, the plots of the original ECG signal are recovered from 88, 104, and 120 sparse coefficients reconstructed on the DWT basis at the compression ratio of 0.2, 0.3, and 0.4, respectively. The graphs 1008, 1010, and 1012 illustrate the corresponding signal reconstruction (RSNR) for each reconstruction as illustrated in graphs 1002, 1004, and 1006, respectively. Note that as more measurements are used in the reconstruction, more sparse coefficients can be reconstructed correctly, and the SNR performance improves. This shows the importance of supporting a large capacity of k to achieve high reconstruction quality. In this sense, the reconstruction engine can be a suitable solution to the accuracy-driven CS based wireless healthcare systems.

Figure 11:
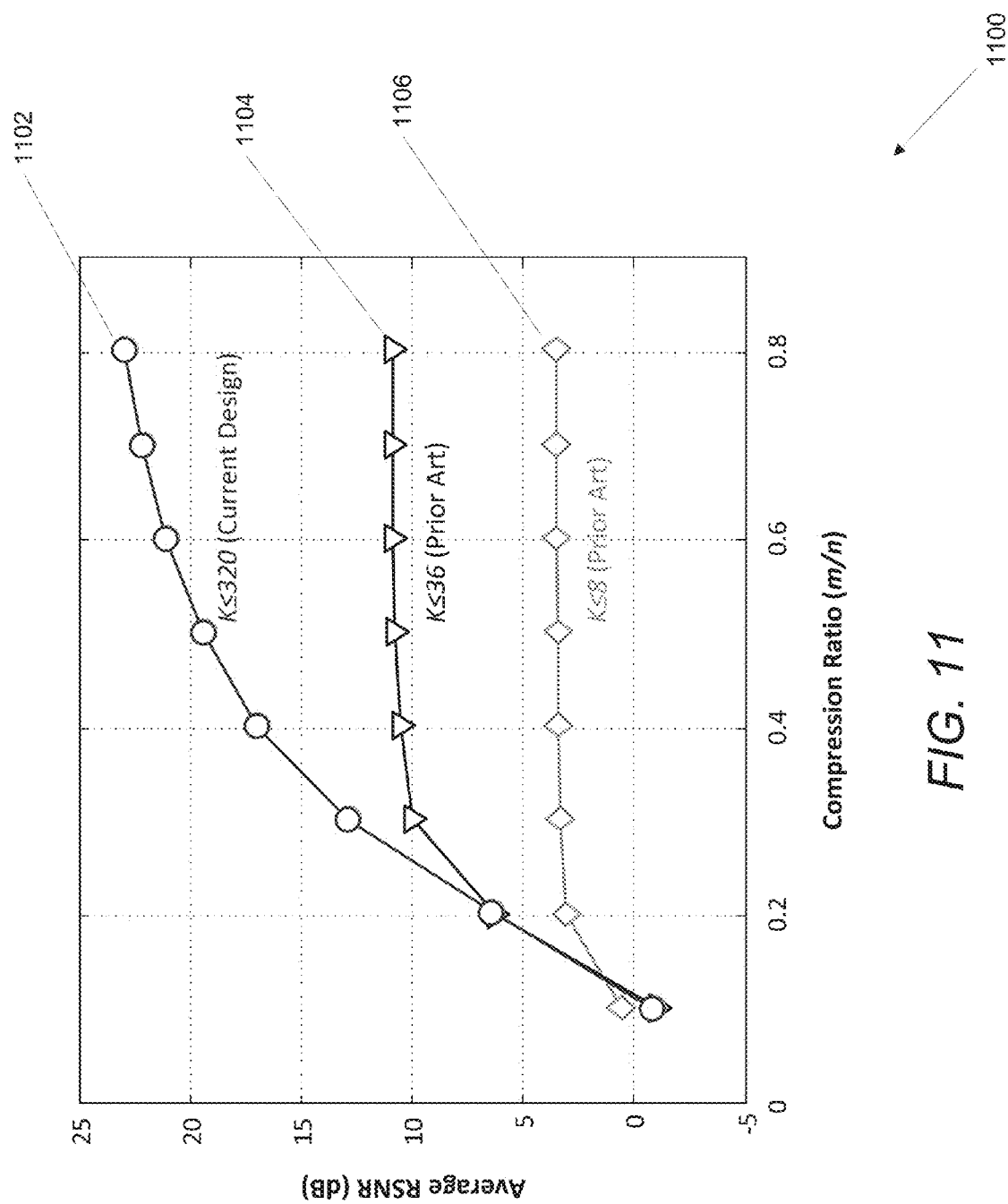
FIG. 11 is graph illustrating projected RSNR performance based on various signal sparsity level (k) in accordance with an embodiment of the invention.

To further illustrate the viability of the reconstruction engine, the same ECG reconstruction test is performed again on the FPGA with limited k values. A graph illustrating projected RSNR performance assuming k is limited to 8, 36, and 320 in accordance with an embodiment of the invention is illustrated in FIG. 11. The graph 1100 depicts the results for the proposed design using k=320 1102, and prior art systems using k=36 1104 and k=8 1106. In many embodiments, with only 8 sparse coefficients allowed in the reconstruction of the ECG signal, the RSNR is limited to 3 dB only. When up to 36 spare coefficients are supported, the RSNR quickly saturates to approximately 10 dB as m increases. Note that such RSNR performance fails to meet the accuracy requirement for many diagnostics applications. Alternatively, the spare coefficient capacity is no longer a limiting factor for the RSNR performance of various designs. Although specific reconstruction accuracy results are discussed above with respect to FIGS. 7-11, any of a variety of reconstruction accuracy tests and analysis as appropriate to the requirements of a specific application can be utilized in accordance with embodiments of the invention. Performance and energy efficiency analysis in accordance with embodiments of the invention are discussed further below.

D. Performance and Energy Efficiency Benchmarking

In order to compare the performance and the energy efficiency of the hardware reconstruction with its software counterpart, general CS reconstruction of ideally sparse signals can be used in benchmarking. First, k-sparse signals $x \in S_k^n$ are generated with different problem size n and sparsity level k. Specifically, for each n and k, 100 signals are randomly generated based on a Normal distribution $\mathcal{N}(0,1)$. Note that the index of the nonzero elements in each signal is also randomly selected. In many embodiments, the generated signals can be sampled by Gaussian random matrices $A \in \mathbb{R}^{m \times n}$, where an empirical value of C=1.8 is used for evaluating the measurement size m according to (7). Then, the sparse signals can be directly recovered using the reconstruction engine on the FPGA and the C program, respectively.

Figure 12:
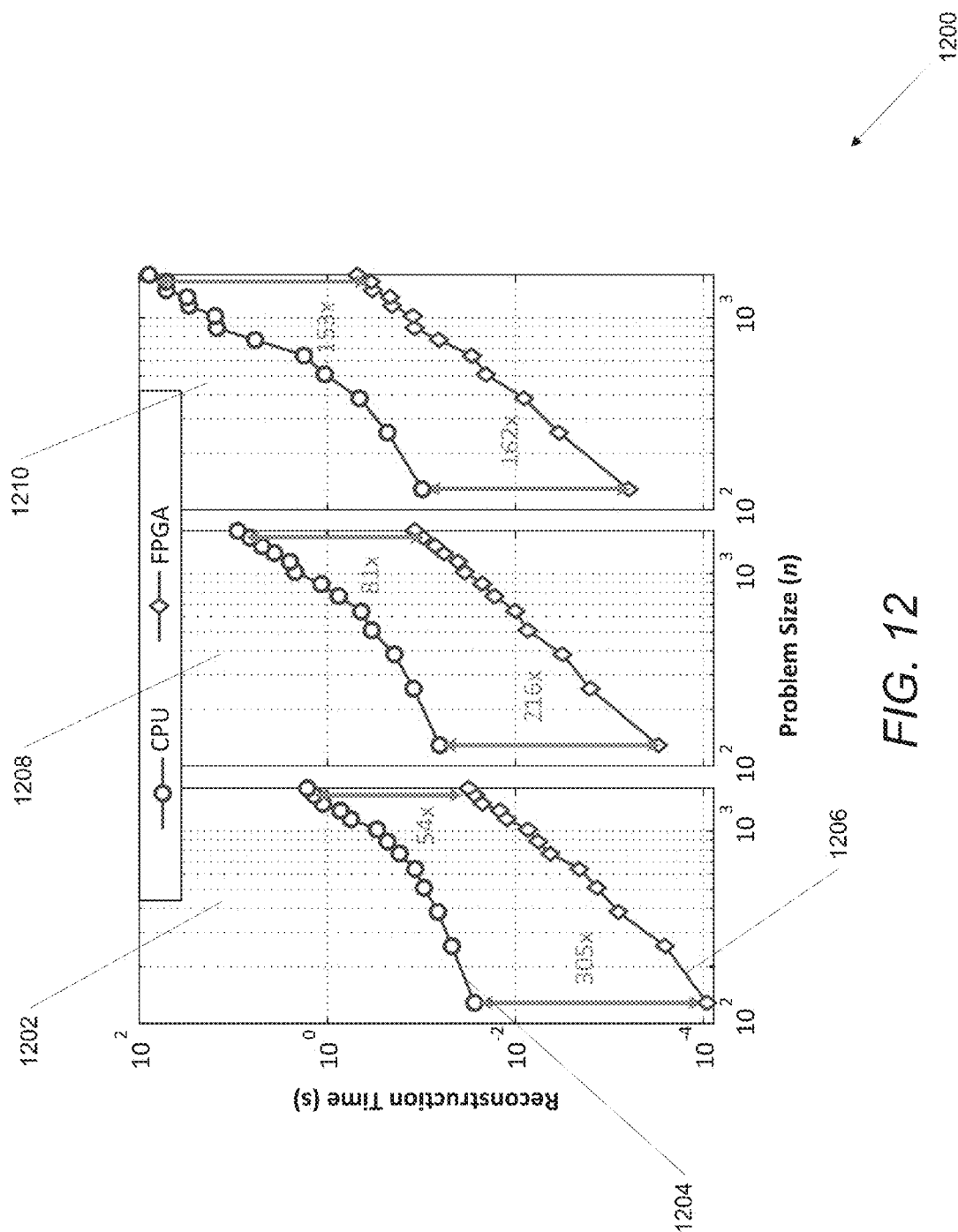
FIG. 12 is graph illustrating variations in averaged FPGA reconstruction time versus CPU run time in accordance with an embodiment of the invention.

A graph illustrating averaged FPGA reconstruction time versus CPU run time measured from different trials in accordance with an embodiment of the invention is illustrated in FIG. 12. As discussed above, OMP typically utilizes intensive memory access. In general purpose computing platforms, accessing data from the main memory has a relatively long latency in case of cache misses. Such long latency will become a dominating factor on the overall performance when the data size that can be pipelined for access is small. Consequently, as n decreases, the reduction in CPU run time slows down gradually. Graph 1200 illustrates a first trial 1202, where the top curve 1204 for the CPU starts to flatten out as n≤800. In contrast, the reconstruction engine on the FPGA curve 1206 has a flattened memory architecture. All the data-path memories are accessible to the vector core at the same level of hierarchy. As a result, the memory access latency is minimized regardless of the access pattern. As further illustrated in the trials depicted in 1208 and 1210, the FPGA reconstruction time drops at a constant rate as n decreases, indicating a good scalability of the proposed architecture. Note that the software performance does not scale as well as the FPGA implementation.

In many embodiments, more iterations of the OMP process are typically performed for recovering $x \in S_k^n$ with higher k. In addition, the computational complexity of the LS task increases quadratically with k (see Table II). FIG. 11 shows that as k increases, the FPGA acceleration becomes less effective when n is small, but more effective when n is large. In various embodiments, for n=100, an average speed-up of 71, 51, and 47 times can be achieved at the k/n ratio of 0.1, 0.2, and 0.3, respectively. In several embodiments, when n=1600, the corresponding speed-up is 48, 76, and 147 times, respectively. The difference comes from how the memory access latency affects the overall performance. When k is small, the complexity of the LS task is limited. The memory access latency affects the overall performance as a fixed overhead. Thus, it becomes less dominating as the complexity of the LS task increases. Differently, when k is large, the memory access latency expands the execution time as a scaling factor. When computing the FS and BS in the LS task, iteratively, each loop of the operation can have strict data dependency on its previous loop. As a result, the total execution time of the LS task can be proportional to the loop latency. In the CPU systems, the loop structure is usually virtualized by reading from and writing to the same memory. Consequently, the memory access latency becomes the bottleneck of the loop latency. Alternatively, the reconstruction engine can have a customized loop structure with a dedicated SRL unit as the feedback path (see FIG. 5B). This provides the scalable loop latency with no memory access involved. Therefore, the FPGA acceleration becomes more effective as the size of the LS task increases at large k.

In the benchmarking, the C program can be powered by a 22 nm Intel Core 2 i7-4700MQ mobile processor, which has a 2.4 GHz operating frequency and a thermal design power of 47 W. The average CPU utilization rate of the C program is recorded as 94% during the reconstruction test. Therefore, the software reconstruction on CPU is estimated to consume an average power of 44.2 W. On the other hand, the FPGA implementation is reported to have a total power consumption of 1.34 W, which is estimated at 53.7 MHz by an XPower Analyzer after placement and route.

Figure 13:
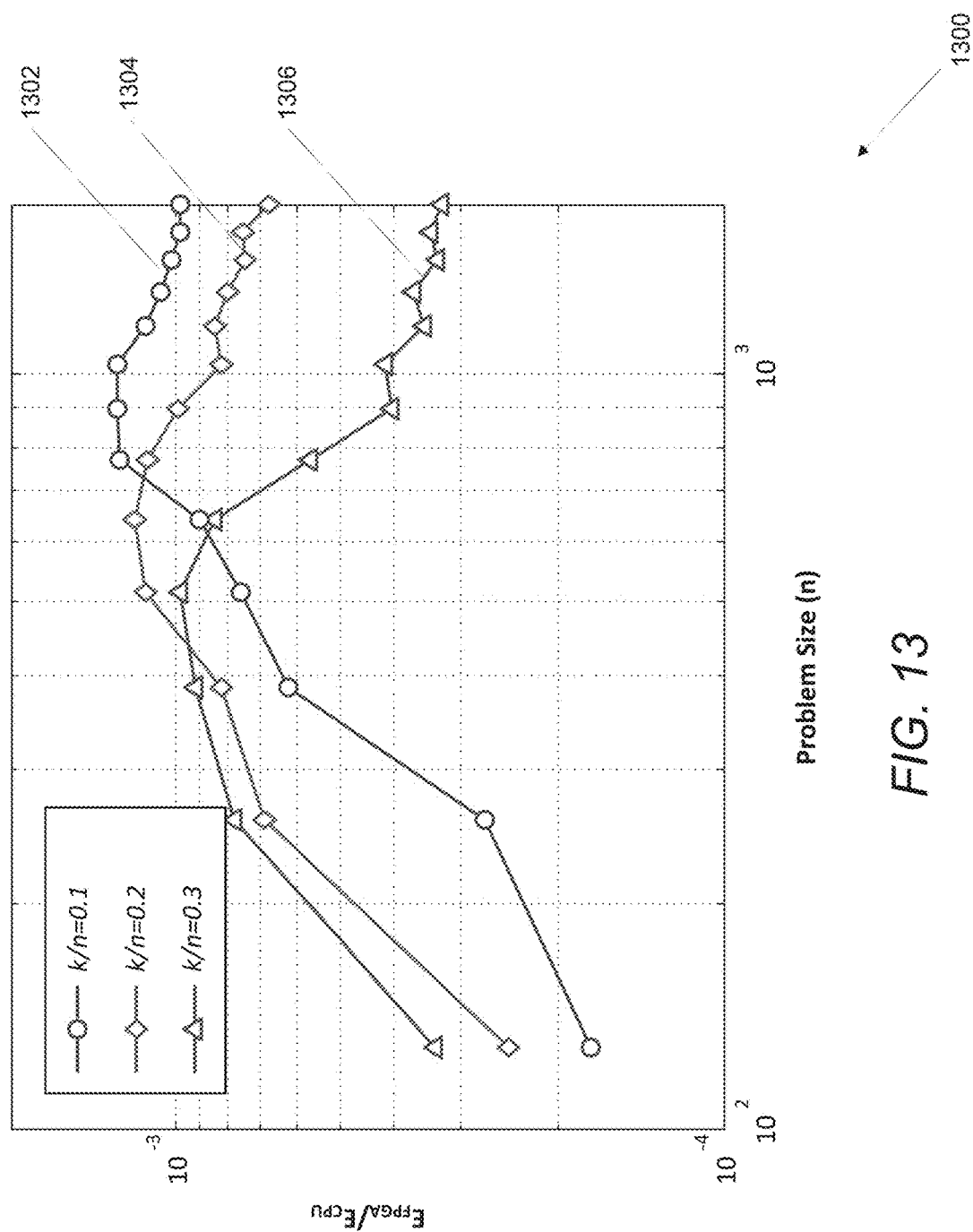
FIG. 13 is graph illustrating total energy consumption of an FPGA during reconstruction in accordance with an embodiment of the invention.

A graph illustrating total energy consumption of an FPGA reconstruction at different problem size n in accordance with an embodiment of the invention is illustrated in FIG. 13. The graph 1300 includes energy consumption for when k/n=0.1 1302, k/n=0.2 1304, and k/n=0.3 1308. In many embodiments, the energy number is calculated as the product of the average reconstruction time and the average power. For comparison purposes, it is normalized to that of the CPU reconstruction. In general, the FPGA implementation can be 3 orders of magnitude more energy-efficient than the software counterpart, especially when the signal has a small dimension or a large dimension but with low sparsity level. Although specific performance and energy efficiency benchmarks are discussed above with respect to FIGS. 12-13, any of a variety of performance and energy efficiency benchmarks as appropriate to the requirements of a specific application can be utilized in accordance with embodiments of the invention.

While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. An integrated circuit architecture for compressive sensing (CS) reconstruction comprising:
    a vector computation core comprising a plurality of processing elements inter-connected in parallel that is dynamically configured to perform vector operations using microcode generated by a global control unit;
    a scalar computation core configured to perform scalar operations, wherein the scalar computation core comprises a comparator, a sequential divider, and a plurality of adders, wherein the vector computation core and the scalar computation core are linked by data-path memories and are configured to cascade in a pipeline as a processing unit and configured to execute correlation sorting, folded inner product, forward substitution, and backward substitution operations;
    a shift register logic configured to provide latency in feedback paths associated with the plurality of processing elements and in a global feedback path between the vector and scalar computation cores, wherein the global feedback path links an adder in the scalar computation core to the plurality of processing elements in the vector computation core into parallel loops configured to execute forward substitution and backward substitution operations;
    a plurality of data-path memories each comprising a memory controller and configured to connect the vector and scalar computation cores, where the plurality of data-path memories are configured to provide data-flow control using the plurality of memory controllers and the plurality of data-path memories comprises:
        at least one data-path memory configured to receive and store CS sampled input data;
        at least one data-path memory configured to store an active set of values;
        at least one data-path memory configured to store a residual error estimate; and
        at least one data-path memory configured to store an estimated output data signal;
    the global control unit that is a finite state machine configured to synchronize and coordinate the plurality of memory controllers and the vector and scalar computation cores to iterate between a plurality of configurations to jointly perform a selective set of vector and scalar operations using:
        a first atom searching configuration of the vector and scalar computation cores, and the plurality of data-path memories in which a single atom is selected by maximizing its correlation coefficients with the residual error estimate and added to the active set of values associated with the estimated output data signal;
        a second least squares solving configuration in which the shift register logic, the vector and scalar computation cores, and the plurality of data-path memories are configured to solve a series of linear equations relating the estimated output data signal to the CS sampled input data to determine updates for the estimated output data signal that minimizes an error measure determined using the updated estimated output data signal and the CS sampled input data; and
        a third estimation update configuration of the vector and scalar computation cores, and the plurality of data-path memories, in which the estimated output data signal estimate is updated based upon the solution to the series of linear equations and the residual error estimate;
    wherein the global control unit is configured to:
        set the residual error estimate to an initial value equal to the CS sampled input data;
        set the plurality of memory controllers of the plurality of data-path memories and the vector and scalar computation cores to their initial states; and
        iterate between the first, second and third configurations until the residual error estimate falls below a predetermined threshold, wherein the computation cores are time-multiplexed using dynamic configuration to iterate between the first, second, and third configurations.

2. The integrated circuit architecture of claim 1, wherein the second least squares solving configuration solves the series of linear equations using a factorization method.

3. The integrated circuit architecture of claim 2, wherein the factorization method is an alternative Cholesky factorization, wherein the Cholesky factorization does not include a square root operation.

4. The integrated circuit architecture of claim 3, wherein Cholesky factorization matrices are updated incrementally by computing at each iteration:

$$L_{t-1}D_{t-1}l_{21}=A_{\Lambda_{t-1}}{}^{T}a_{\varphi}$$

and $$d_{22}=a_{\varphi}{}^{T}a_{\varphi}-l_{21}{}^{T}D_{t-1}l_{21}$$

wherein $l_{21} \in \mathbb{R}^{t-1}$ is a column vector and $d_{22}$ is a scalar.

5. The integrated circuit architecture of claim 1, wherein the selective set of scalar operations includes scalar comparison, addition, subtraction, accumulation, and division operations.

6. The integrated circuit architecture of claim 1, wherein the selective set of vector operations includes element-wise vector addition, multiplication, accumulation, multiply-accumulation, vector-scalar product, and inner product operations.

7. The integrated circuit architecture of claim 1, wherein the plurality of data-path memories each comprising a memory controller and configured to connect the vector and scalar computation cores further comprises:
    at least one data-path memory configured to receive and store CS sampling matrix;
    at least one data-path memory configured to receive and store Cholesky factorization matrices; and
    at least one data-path memory configured to receive and store intermediate results.

8. The integrated circuit architecture of claim 1, wherein the global control unit is further configured to issue corresponding operation codes according to configurations to the plurality of memory controllers of the plurality of data-path memories and the vector and scalar computation cores.

9. A method for compressive sensing (CS) reconstruction comprising:
selecting a single atom by maximizing its correlation coefficients with a residual error estimate and adding the selected single atom to an active set of values associated with an estimated output data signal using a first atom searching configuration of a vector computation core, a scalar computation core, and a plurality of data-path memories, wherein:
the vector computation core comprises a plurality of processing elements inter-connected in parallel that is dynamically configured to perform vector operations using microcode generated by a global control unit;
the scalar computation core is configured to perform scalar operations, wherein the scalar computation core comprises a comparator, a sequential divider, and a plurality of adders, wherein the vector computation core and the scalar computation core are linked by data-path memories and are configured to cascade in a pipeline as a processing unit and configured to execute correlation sorting, folded inner product, forward substitution, and backward substitution operations;
the plurality of data-path memories each comprising a memory controller and configured to connect the vector and scalar computation cores, where the plurality of data-path memories are configured to provide data-flow control using the plurality of memory controllers and the plurality of data-path memories comprises:
at least one data-path memory configured to receive and store CS sampled input data;
at least one data-path memory configured to store the active set of values;
at least one data-path memory configured to store the residual error estimate; and
at least one data-path memory configured to store the estimated output data signal;
solving a series of linear equations relating the estimated output data signal to the CS sampled input data to determine updates for the estimated output data signal that minimizes an error measure determined utilizing the updated estimated output data signal and the CS sampled input data using a second least squares solving configuration of a shift register logic, the vector and scalar computation cores, and the plurality of data-path memories, wherein:
the shift register logic is configured to provide latency in feedback paths associated with the plurality of processing elements and in a global feedback path between the vector and scalar computation cores, wherein the global feedback path links an adder in the scalar computation core to the plurality of processing elements in the vector computation core into parallel loops configured to execute forward substitution and backward substitution operations;
updating the estimated output data signal estimate based upon the solution to the series of linear equations and the residual error estimate using a third estimation update configuration of the vector and scalar computation cores, and the plurality of data-path memories;
wherein the global control unit that is a finite state machine is configured to:
synchronize and coordinate the plurality of memory controllers and the vector and scalar computation cores to iterate between a plurality of configurations to jointly perform a selective set of vector and scalar operations;
set the residual error estimate to an initial value equal to the CS sampled input data;
set the plurality of memory controllers of the plurality of data-path memories and the vector and scalar computation cores to their initial states; and
iterate between the first, second and third configurations until the residual error estimate falls below a predetermined threshold, wherein the computation cores are time-multiplexed using dynamic configuration to iterate between the first, second, and third configurations.

10. The method of claim 9, wherein the second least squares solving configuration solves the series of linear equations using a factorization method.

11. The method of claim 10, wherein the factorization method is an alternative Cholesky factorization, wherein the Cholesky factorization does not include a square root operation.

12. The method of claim 11, wherein Cholesky factorization matrices are updated incrementally by computing at each iteration:

$$L_{t-1}D_{t-1}l_{21}=A_{\Lambda_{t-1}}^T a_\varphi$$

and $$d_{22}=a_\varphi^T a_\varphi - l_{21}^T D_{t-1} l_{21}$$

wherein $l_{21} \in \mathbb{R}^{t-1}$ is a column vector and $d_{22}$ is a scalar.

13. The method of claim 9, wherein the selective set of scalar operations includes scalar comparison, addition, subtraction, accumulation, and division operations.

14. The method of claim 9, wherein the selective set of vector operations includes element-wise vector addition, multiplication, accumulation, multiply-accumulation, vector-scalar product, and inner product operations.

15. The method of claim 9, wherein the plurality of data-path memories each comprising a memory controller and configured to connect the vector and scalar computation cores further comprises:
at least one data-path memory configured to receive and store CS sampling matrix;
at least one data-path memory configured to receive and store Cholesky factorization matrices; and
at least one data-path memory configured to receive and store intermediate results.

16. The method of claim 9, wherein the global control unit is further configured to issue corresponding operation codes according to configurations to the plurality of memory controllers of the plurality of data-path memories and the vector and scalar computation cores.

* * * * *